United States Patent [19]

Green

[11] 4,354,628

[45] Oct. 19, 1982

[54] SURGICAL STAPLER APPARATUS HAVING PIVOTALLY RELATED STAPLE HOLDER AND ANVIL

[75] Inventor: David T. Green, Norwalk, Conn.

[73] Assignee: United States Surgical Corporation, Norwalk, Conn.

[21] Appl. No.: 188,691

[22] Filed: Sep. 29, 1980

[51] Int. Cl.³ .............................................. B25C 1/00
[52] U.S. Cl. ...................................... 227/19; 227/152; 227/156; 227/DIG. 1; 128/334 R
[58] Field of Search ............. 128/334 R; 227/DIG. 1, 227/19, 120, 135, 152, 156

[56] References Cited

U.S. PATENT DOCUMENTS

| | | | |
|---|---|---|---|
| 2,344,071 | 3/1944 | Wilson et al. | 1/49.1 |
| 3,017,637 | 1/1962 | Sampson | 1/50 |
| 3,080,564 | 3/1963 | Strekopitov et al. | 1/50 |
| 3,252,643 | 5/1966 | Strekopytov et al. | 227/109 |
| 3,269,630 | 8/1966 | Fleischer | 227/107 |
| 3,275,211 | 9/1966 | Hirsch et al. | 227/124 |
| 3,315,863 | 4/1967 | O'Dea | 227/19 |
| 3,494,533 | 2/1970 | Green et al. | 227/19 |
| 3,551,987 | 1/1971 | Wilkinson | 227/DIG. 1 |
| 3,589,589 | 6/1971 | Akopov | 227/153 |
| 3,692,224 | 9/1972 | Astafiev et al. | 227/19 |
| 3,795,034 | 3/1974 | Strekopytov et al. | 29/212 D |
| 3,935,981 | 2/1976 | Akopov et al. | 227/19 |
| 4,111,206 | 9/1978 | Vishnevsky et al. | 128/305 |
| 4,216,891 | 8/1980 | Behlke | 227/30 |
| 4,272,002 | 6/1981 | Moshofsky | 227/19 |

FOREIGN PATENT DOCUMENTS 406832 12/1924 Fed. Rep. of Germany .
1276239 6/1972 United Kingdom .

Primary Examiner—Paul A. Bell
Attorney, Agent, or Firm—Robert R. Jackson; John E. Nathan

[57] ABSTRACT

Surgical stapler apparatus for forming an array of surgical staples in body tissue includes an anvil member against which the staples are crimped and a staple holder pivotally mounted adjacent one end of the anvil member so that the staple holder tends to displace with any displacement of the anvil member during use to substantially reduce relative displacement of the anvil member and staple holder and thereby assure proper alignment of these two elements.

33 Claims, 23 Drawing Figures

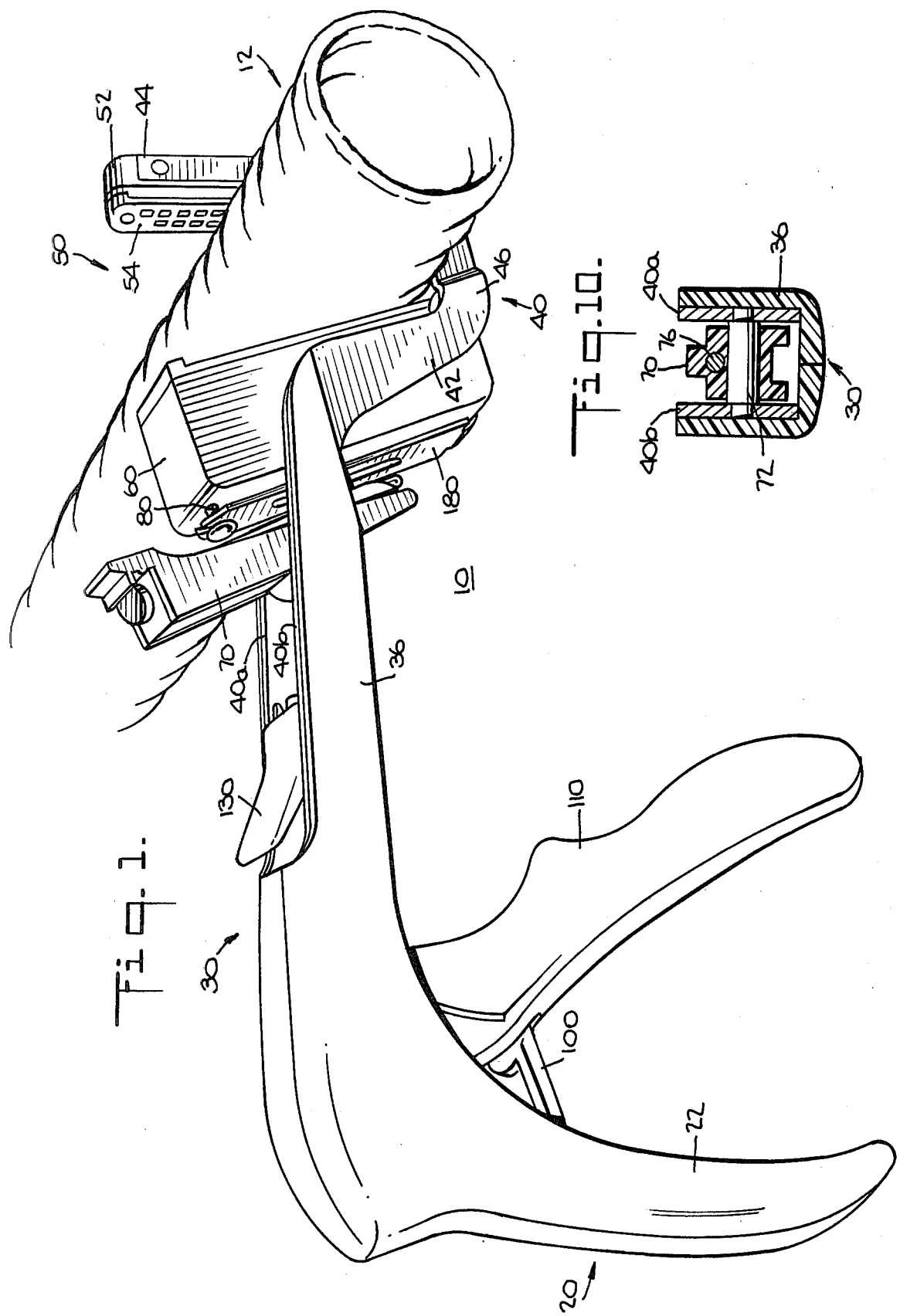

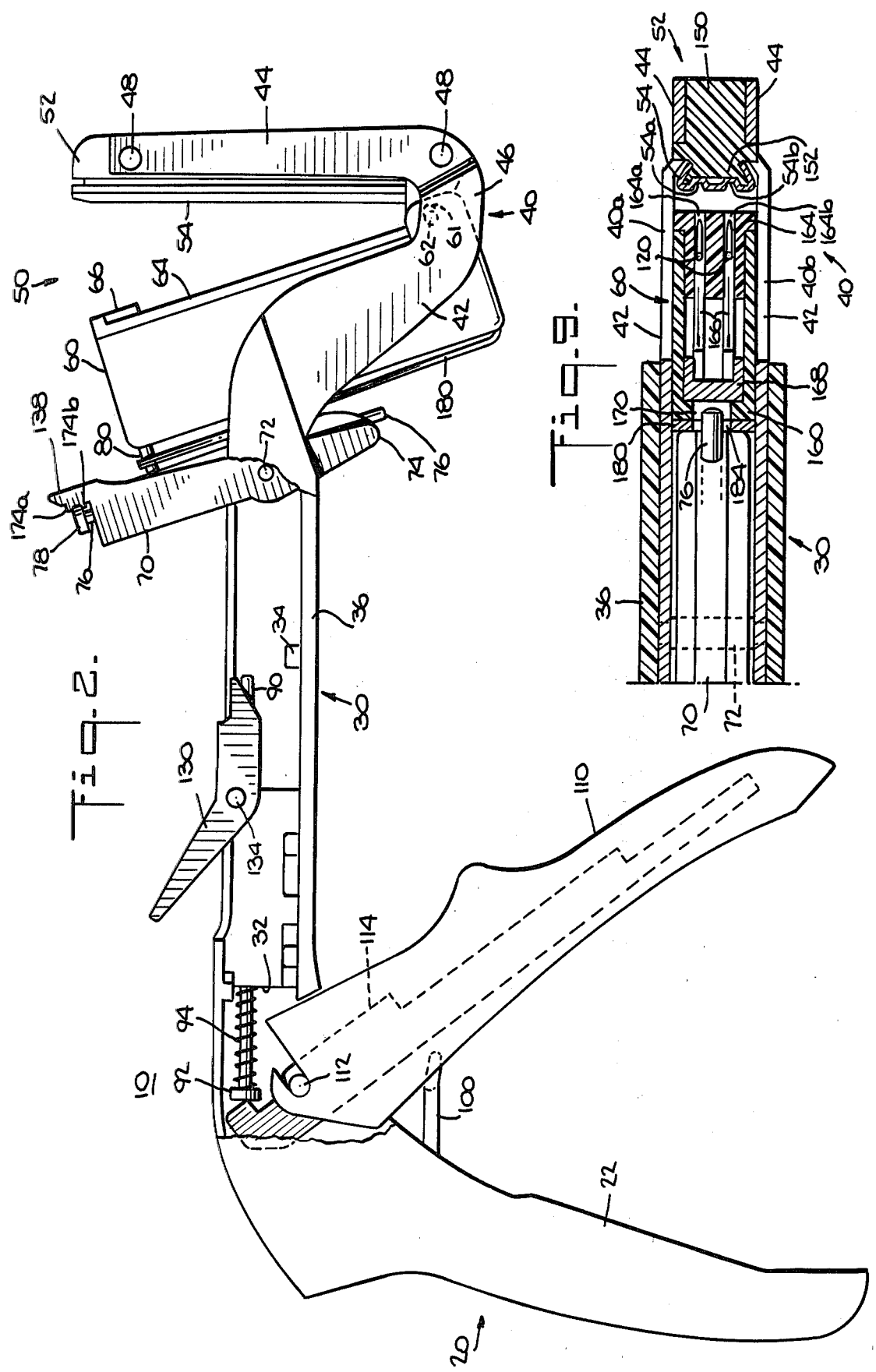

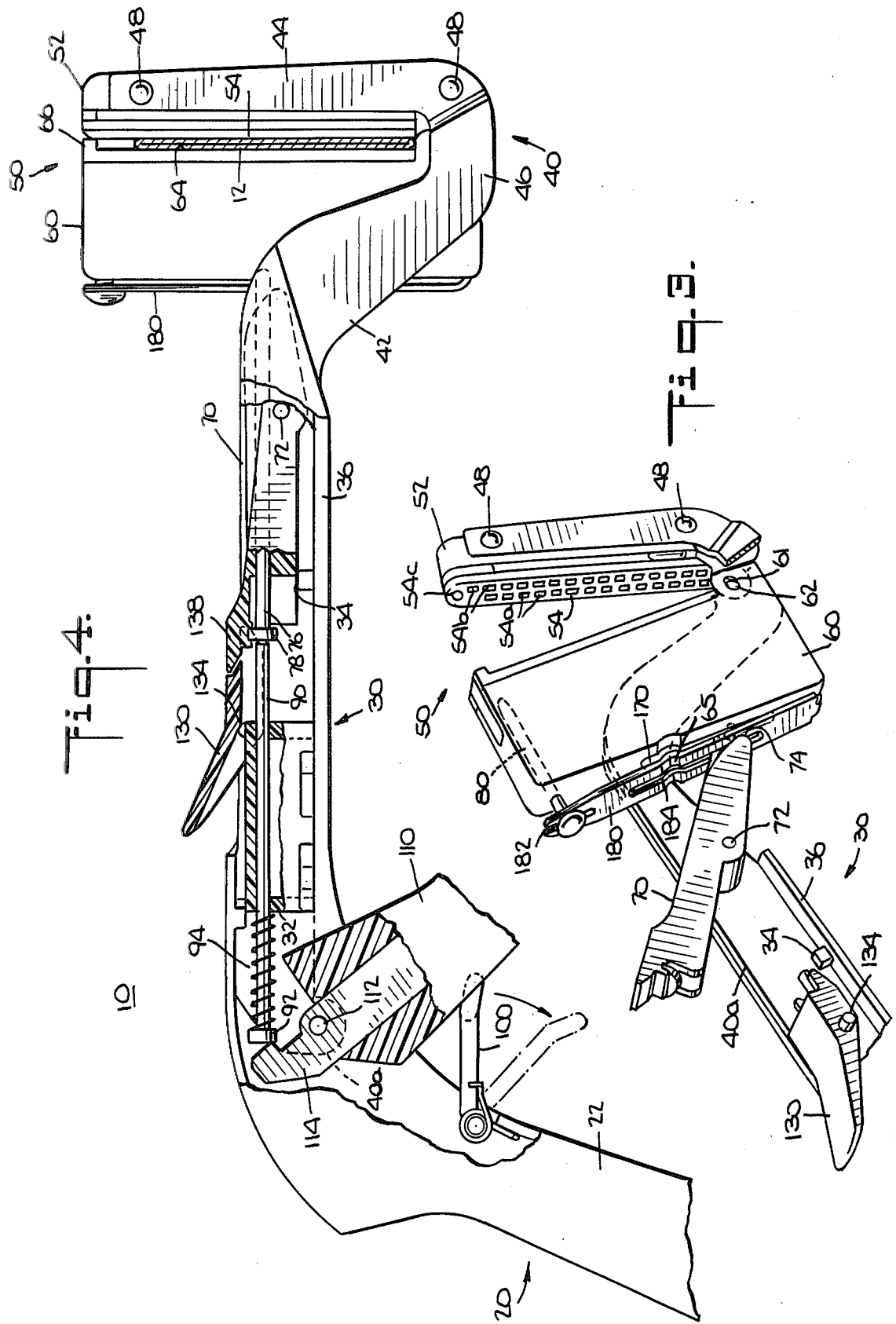

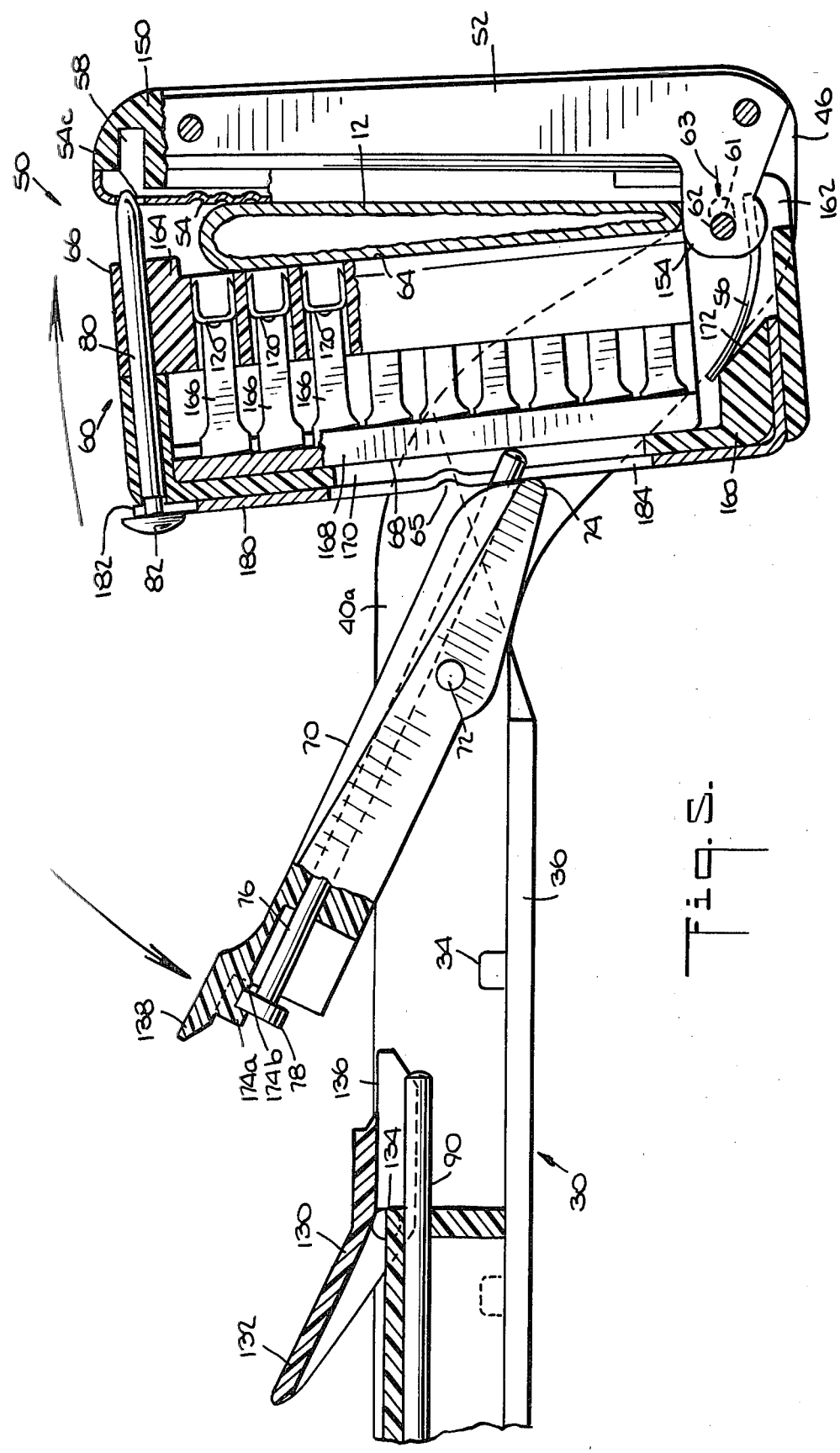

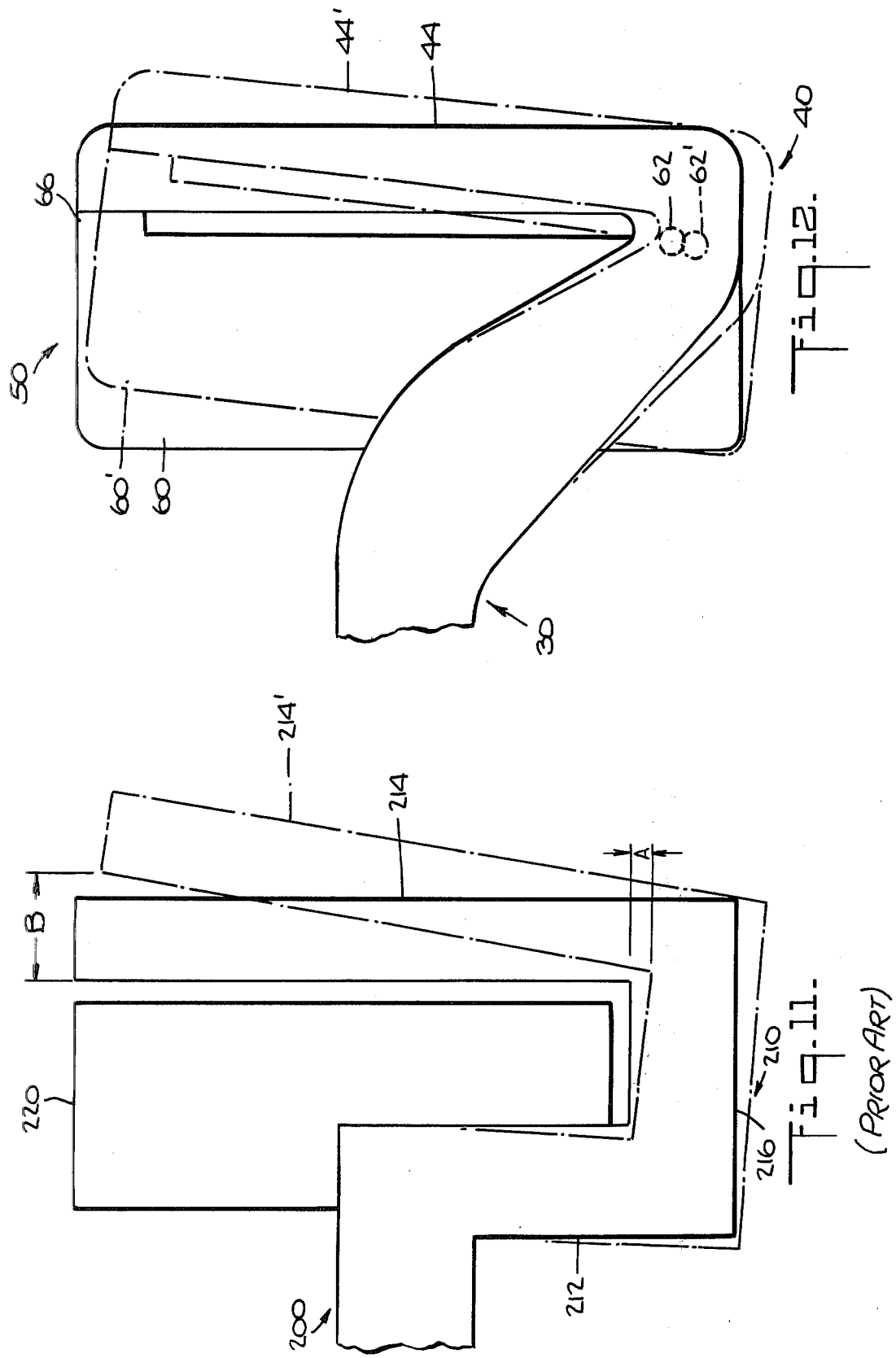

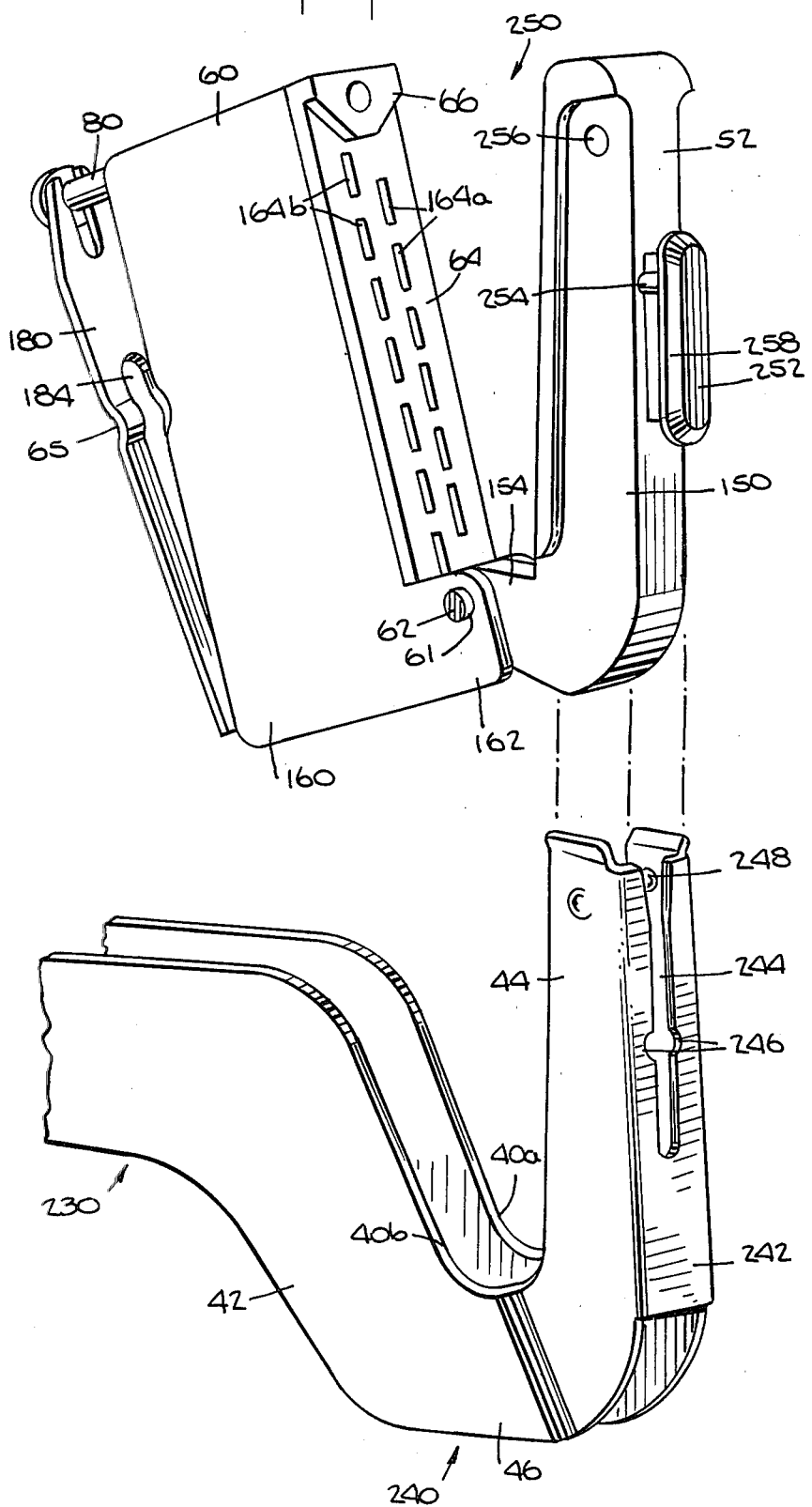

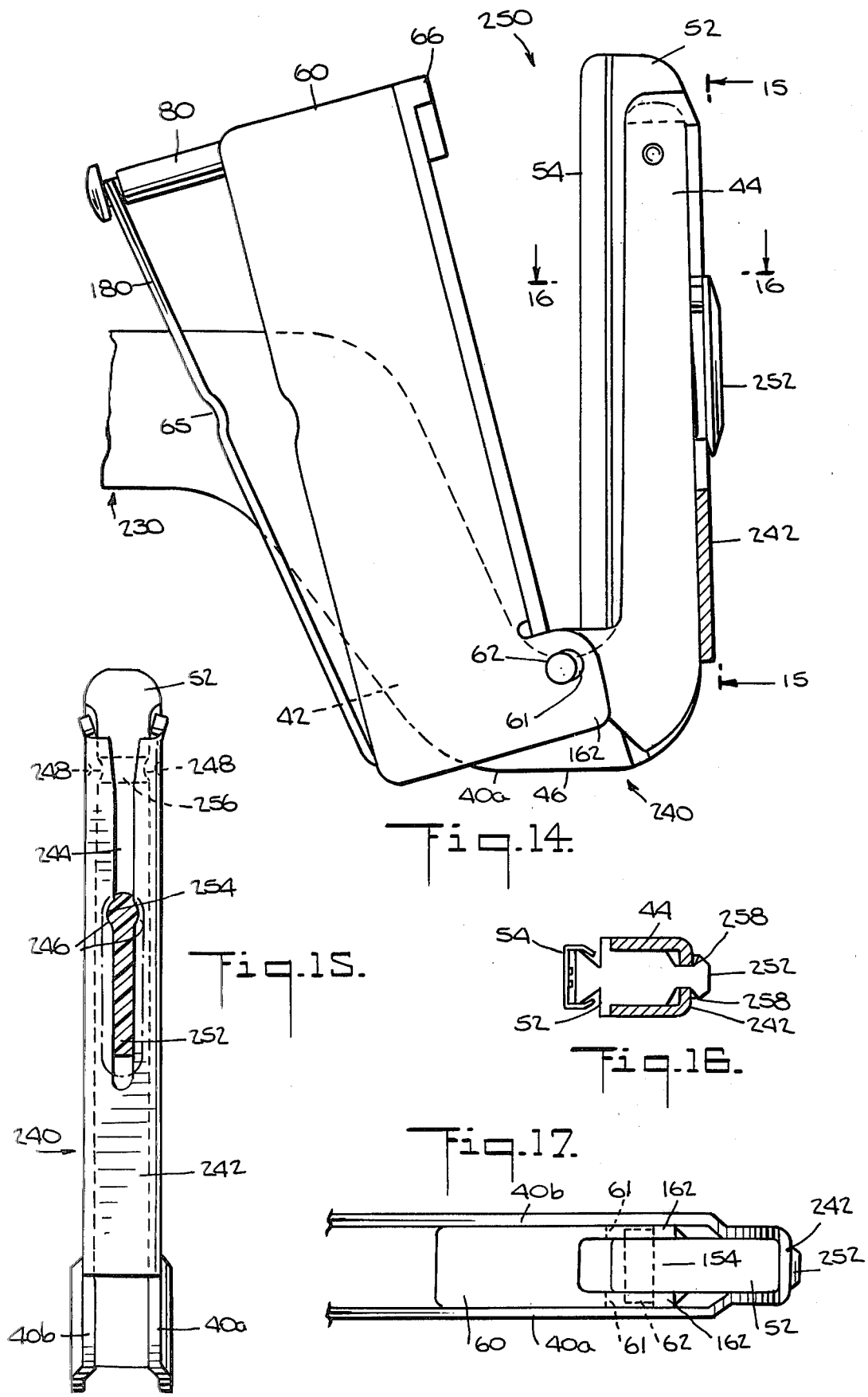

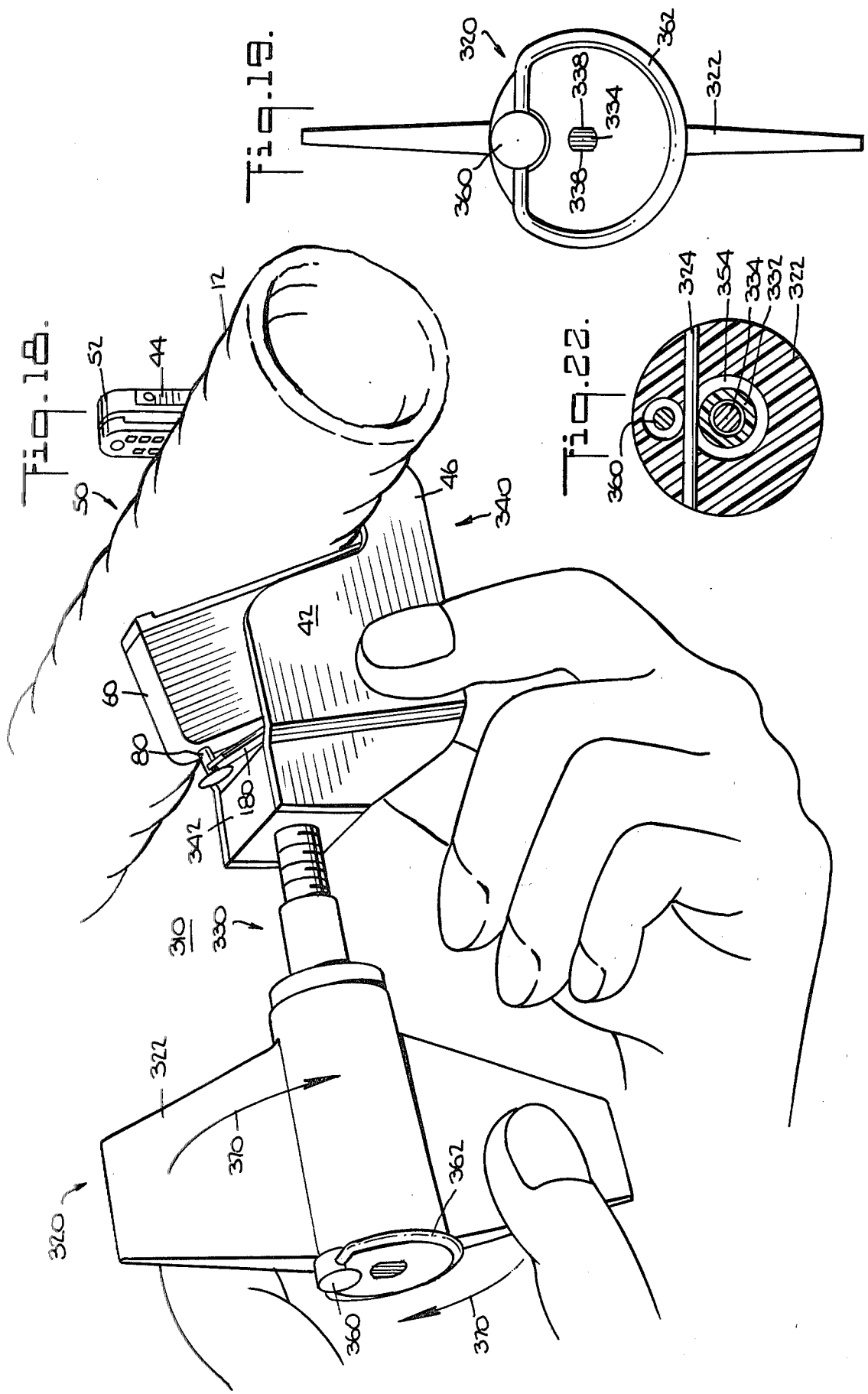

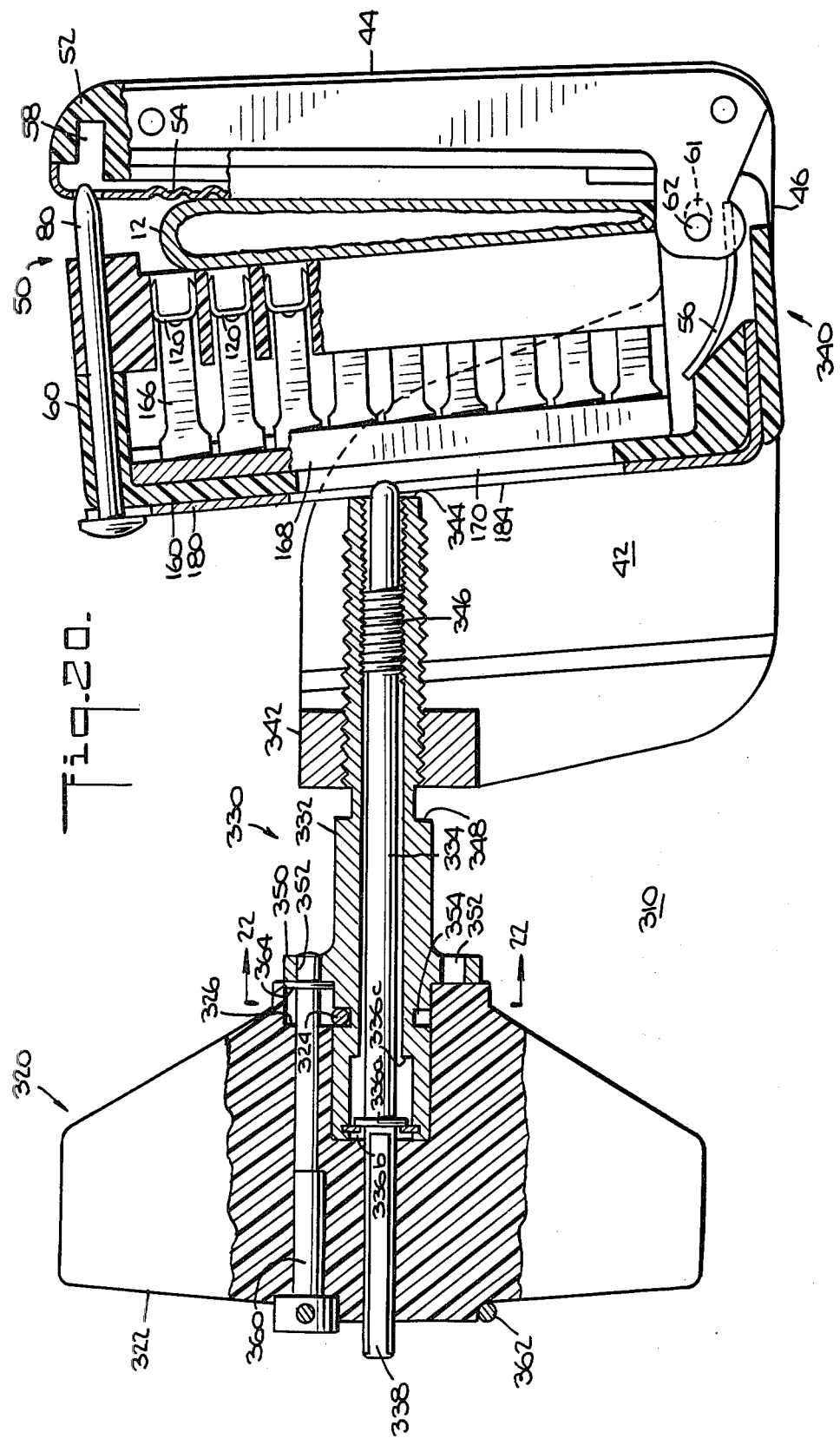

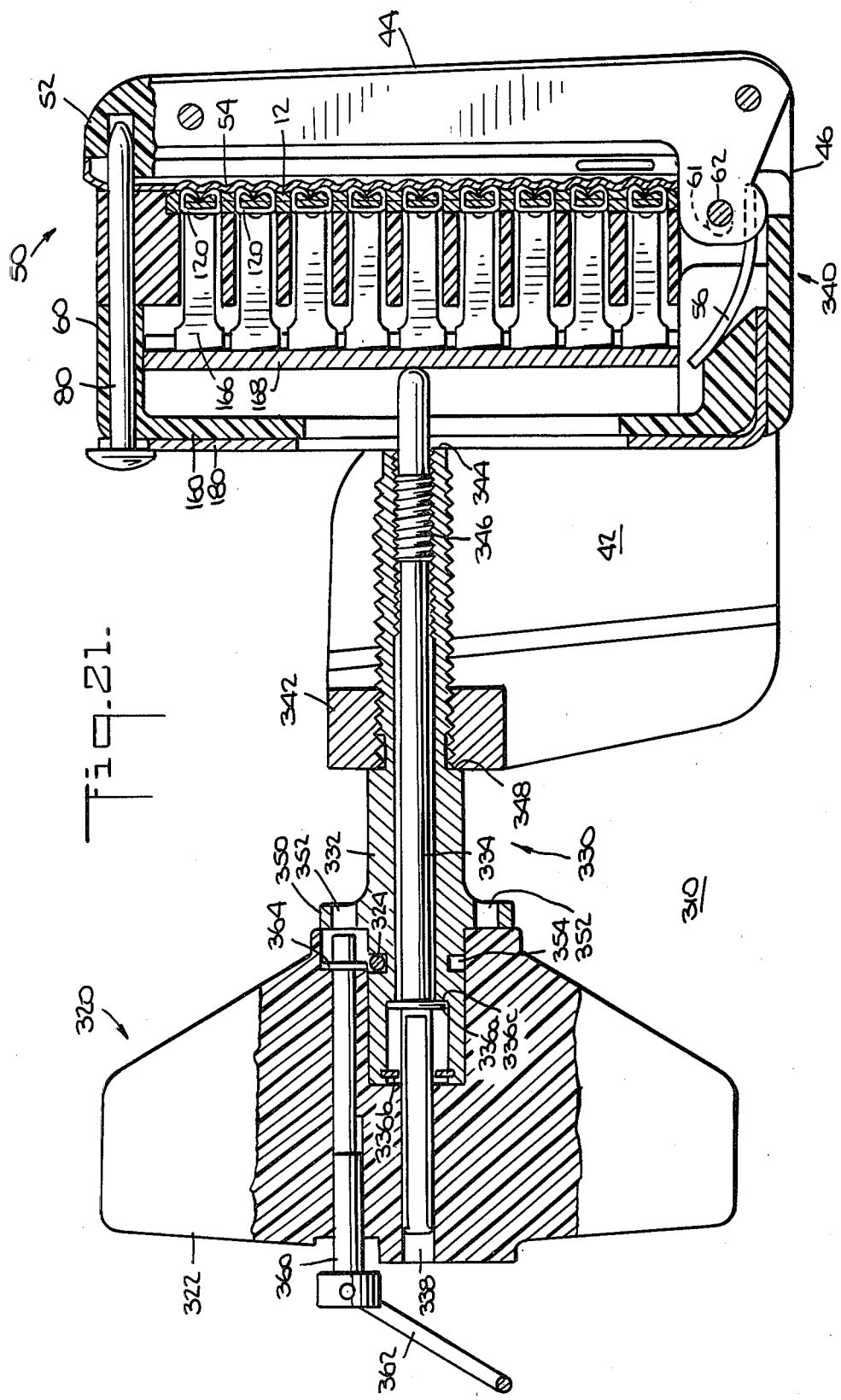

SURGICAL STAPLER APPARATUS HAVING PIVOTALLY RELATED STAPLE HOLDER AND ANVIL

BACKGROUND OF THE INVENTION

This invention relates to surgical stapling apparatus, and more particularly to surgical stapling apparatus for substantially simultaneously driving a plurality of surgical staples through body tissue and against an anvil to produce an array of crimped staples in the body tissue.

Surgical staplers in which a plurality of surgical staples are driven substantially simultaneously from a staple holder to produce an array of staples in body tissue are known. Typically these staplers include a staple holder disposed on one side of the tissue to be stapled, an anvil parallel to the staple holder on the other side of the tissue to be stapled, means for linearly translating the staple holder and the anvil toward one another so that the tissue is clamped between them, and means for driving the staples from the staple holder so that the ends of the staples pass through the tissue and are crimped against the anvil, therey producing an array of finished staples in the tissue. In common use are staplers in which the staple holder and anvil comprise a disposable cartridge removably mounted in or on a permanent actuator for supporting and actuating the cartridge. The cartridge is disposable after a single use. The permanent actuator is reusable in the same surgical procedure after reloading with a fresh cartridge, and is reusable in another surgical procedure after cleaning, sterilizing, and reloading.

Because of the difficulty and expense of cleaning and sterilizing surgical instruments, there is increasing interest in and demand for disposable surgical instruments. This is especially true of surgical instruments having a number of moving parts such as the surgical stapler actuators mentioned above. On the other hand, the actuators in prior surgical staplers have generally been required to withstand relatively large forces associated with clamping the tissue to be stapled and driving a plurality of staples through the tissue, while at the same time providing the precise alignment between the staple holder and anvil which is required for proper staple formation. These requirements have typically necessitated very rigid actuator structures including substantial numbers of precision parts made of relatively expensive materials such as stainless steel. Such structures are generally not economically disposable.

It is therefore an object of this invention to provide surgical stapling apparatus of the type described above in which the requirements for rigidity and precision in the actuator are substantially relaxed so that the actuator can be made using a higher proportion of relatively inexpensive materials and in a relatively inexpensive design, thereby making the actuator (as well as the cartridge) economically disposable if desired.

Although instruments of the type described above are available for performing several different types of surgical stapling procedures requiring instruments and staple arrays of various configurations, an illustrative type of instrument is the so-called thoracic-abdominal surgical stapler, which is typically used for forming a row of staples laterally through hollow body organs such as the thorax, trachea, stomach, or intestines. Staplers of this type generally have a U-shaped structure at the distal end of the instrument which is positioned around the tissue to be stapled. The anvil, which in this type of instrument is a longitudinal member, is mounted on the distal leg of the U-shaped structure, while the staple holder is mounted relative to the proximal leg of the structure. A knob at the proximal end of the instrument allows the staple holder to be translated toward the anvil to clamp the tissue between the opposing faces of the anvil and the staple holder. Thereafter, a handle mechanism also associated with the proximal portion of the instrument is operated to simultaneously drive all of the staples out of the staple holder through the tissue and against the anvil. When the tissue has thus been stapled, the clamping knob is operated again to retract the now empty staple holder, thereby releasing the tissue from the instrument.

A problem associated with instruments of this type (and to various degrees with other similar types of surgical staplers) is that the large forces acting on the U-shaped structure at the distal end of the instrument as a result of clamping the tissue in that structure and simultaneously driving a large number of staples between the parallel legs of that structure can cause the structure to deform. In particular, the parallel legs of the U-shaped structure may be forced apart and thereby lose their parallelism. The distal leg of the U-shaped structure may also be shifted longitudinally relative to the proximal leg as a result of deformations in the base of the U-shape and elsewhere in the structure. These deformations or strains in the U-shaped structure can occasionally cause the staple holder and the anvil to become misaligned to such a degree that the anvil no longer crimps some or all of the staples properly. The improperly crimped staples may not adequately staple the tissue and/or may injure the tissue.

It is therefore another object of this invention to provide surgical stapling apparatus of the type described above in which misalignment of the staple holder and anvil due to deformation of the associated support structure is substantially reduced or eliminated.

SUMMARY OF THE INVENTION

These and other objects of the invention are accomplished in accordance with the principles of the invention by providing surgical stapler apparatus in which the staple holder is pivotally mounted relative to the anvil so that the staple holder travels with the anvil during any deformations or deflections of the anvil and is thereby always properly aligned with the anvil. Proper alignment between the staple holder and anvil is thereby maintained primarily by these elements themselves. A high degree of rigidity and precision in the remainder of the apparatus (i.e., the actuator portion of the apparatus) is therefore less important, and that portion of the apparatus can be made of less expensive materials and with less stringent manufacturing tolerances. This substantially reduces the cost of the apparatus, making it possible to produce the apparatus as an economically disposable item if desired.

Further features of the invention, its nature and various advantages will be more apparent from the accompanying drawing and the following detailed description of the invention.

BRIEF DESCRIPTION OF THE DRAWING

FIG. 1 is a perspective view of a first illustrative embodiment of thoracic-abdominal surgical stapler apparatus constructed in accordance with the invention.

FIG. 2 is an elevational view, partly cut away, of the apparatus of FIG. 1 prior to use.

FIG. 3 is a perspective view, partly cut away, of a part of the apparatus of FIG. 1 prior to use.

FIG. 4 is a view similar to FIG. 2 showing the apparatus in use with tissue clamped and ready for stapling.

FIG. 5 is an enlarged elevational sectional view of a part of the apparatus of FIG. 1 showing how the apparatus is operated to clamp the tissue to be stapled.

FIG. 9 is a sectional view taken along the line 9—9 in FIG. 6.

FIG. 10 is a sectional view taken along the line 10—10 in FIG. 6.

FIG. 11 is a simplified elevational view of a portion of typical prior art thoracic-abdominal surgical stapler apparatus illustrating the type of structural deformations which may occur in such apparatus during use.

FIG. 12 is a simplified elevational view of a portion of thoracic-abdominal surgical stapler apparatus constructed in accordance with the principles of this invention illustrating the type of structural deformations which may occur in such apparatus during use.

FIG. 13 is a perspective view of a part of a second illustrative embodiment of thoracic-abdominal surgical stapler apparatus constructed in accordance with the invention.

FIG. 14 is an elevational sectional view of the apparatus of FIG. 13.

FIG. 15 is a sectional view taken along the line 15—15 in FIG. 14.

FIG. 16 is a sectional view taken along the line 16—16 in FIG. 14.

FIG. 17 is a view of the bottom of the apparatus shown in FIG. 14.

FIG. 18 is a perspective view of a third illustrative embodiment of thoracic-abdominal surgical stapler apparatus constructed in accordance with the invention.

FIG. 19 is an end view of the apparatus of FIG. 18.

FIG. 20 is an elevational sectional view of the apparatus of FIG. 18 showing operation of the apparatus to clamp the tissue in the stapler.

FIG. 21 is a view similar to FIG. 20 showing operation of the apparatus to staple the clamped tissue.

FIG. 22 is a sectional view taken along the line 22—22 in FIG. 20.

DETAILED DESCRIPTION OF THE INVENTION

Figure 6:
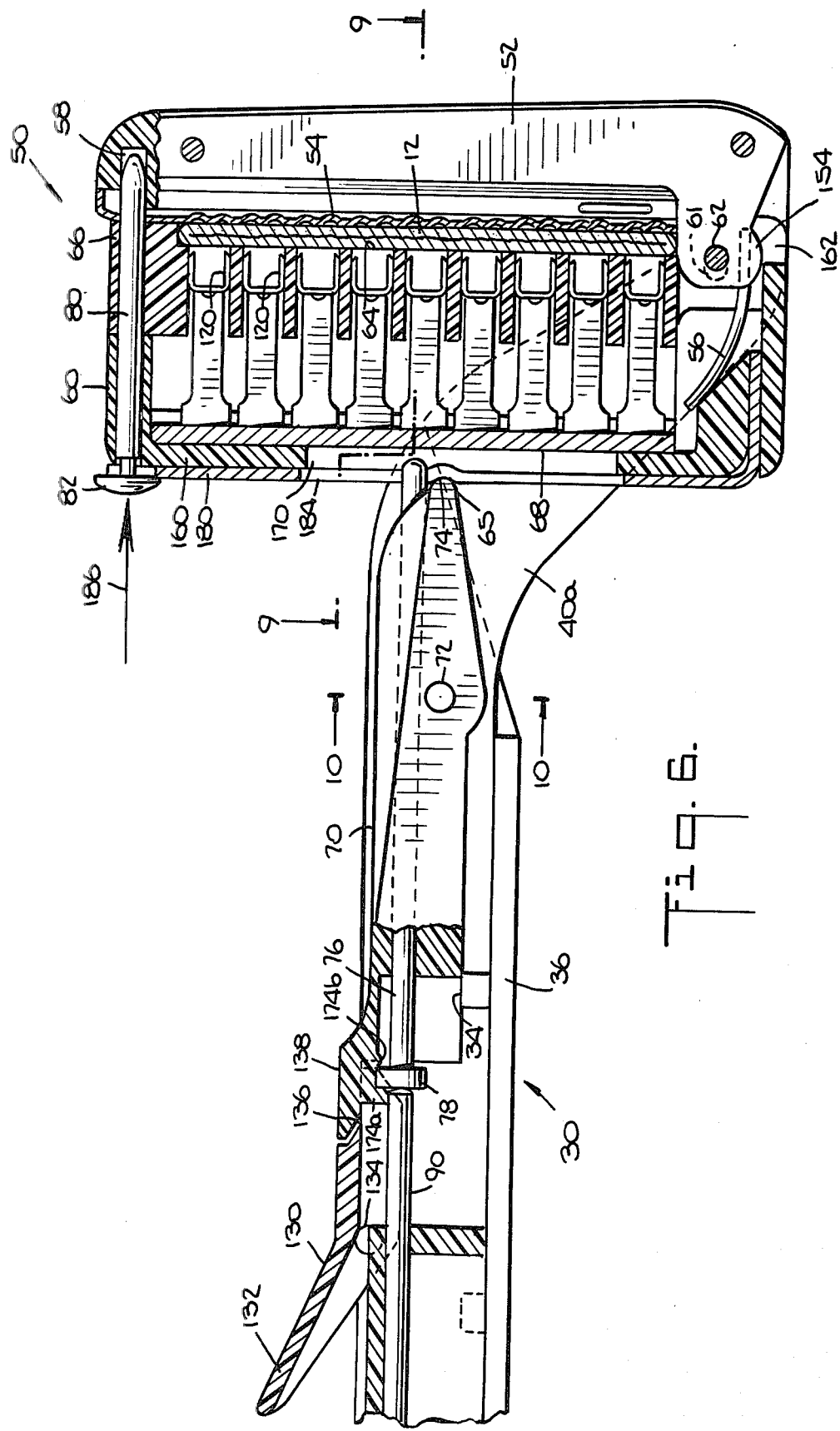
FIG. 6 is a view similar to FIG. 5 showing the condition of the apparatus with the tissue clamped and ready to be stapled.

Although the principles of the invention are applicable to other similar types of surgical stapler apparatus, the invention will be clearly understood from an explanation of its application to thoracic-abdominal surgical stapler apparatus of the type mentioned above. The invention is also applicable to both permanent and disposable apparatus. Accordingly, the invention will first be illustrated in a totally disposable embodiment. Later, a second illustrative embodiment in which a disposable cartridge comprising a staple holder and an anvil is mounted in a permanent instrument will be described. And finally, a third illustrative embodiment which is again totally disposable but which has a different actuator for the staple holder and anvil assembly will be described.

I. First Illustrative Embodiment: Disposable Instrument with Lever Operated Actuator

A. Overall Construction and Operation

FIGS. 1–10 show a first illustrative embodiment of the invention in which the entire apparatus is disposable after use in a single surgical stapling procedure and in which the apparatus is lever actuated.

As shown for example in FIG. 1, illustrative instrument 10 includes handle 20 adjacent the proximal end of the instrument, a longitudinal connecting structure 30 substantially perpendicular to handle 20, and an open U-shaped or V-shaped support structure 40 at the distal end of connecting structure 30. As is better seen in FIG. 2, support structure 40 comprises a proximal leg 42, a distal leg 44, and a base 46 joining one end of each of legs 42 and 44. Support structure 40 lies in a plane substantially parallel to the longitudinal axis of connecting structure 30. The longitudinal axis of each of legs 42 and 44, however, is transverse to the longitudinal axis of connecting structure 30. In use, the instrument is positioned relative to the tissue 12 to be stapled (e.g., a tubular organ such as the thorax) so that the tissue is generally between legs 42 and 44 and transverse to the plane of support structure 40.

As is more clearly seen in FIG. 2, a pivoting staple holder and anvil assembly 50 is mounted on the distal leg 44 of support structure 40. Assembly 50 includes an anvil portion 52 rigidly mounted on leg 44, and a staple holder portion 60 pivotally mounted on anvil portion 52 by means of pivotal axis 62 adjacent the base 46 of support structure 40. (Although pivotal axis 62 may allow solely pivotal motion, in the preferred embodiment shown in the drawing the arrangement of pivotal axis 62 also allows a limited amount of motion of the staple holder perpendicular to the staple holder surface 64 opposite the anvil as described in detail below. This is the function of elongated aperture 61 shown in broken lines in FIG. 2. For purposes of the immediate overall description of the apparatus, however, it will be sufficient to assume that pivotal axis 62 allows purely pivotal motion.) Anvil member 54 is mounted on anvil portion 52 so that it faces staple holder 60. Except for pivotal axis 62, staple holder 60 is otherwise unsupported in the apparatus, although it is guided between the two substantially parallel plates 40a and 40b which make up support structure 40 (see FIG. 9). Staple holder 60 is normally biased away from anvil 54 by leaf spring 56 (FIG. 5) between elements 52 and 60. In the normally open position shown in FIG. 2, assembly 50 can readily receive tissue 12 to be stapled between anvil 54 and the opposite face 64 of staple holder 60 (see also FIG. 1).

When the tissue is in place between anvil 54 and staple holder 60, pivoting clamp actuator 70 is pivoted counter-clockwise about its pivotal axis 72 as shown in FIG. 5. This causes camming surface 74 on the distal end of actuator 70 to pivot staple holder 60 clockwise about its pivotal axis 62, thereby gradually clamping tissue 12 between anvil 54 and the opposing surface 64 of staple holder 60.

When actuator 70 has been fully pivoted counter-clockwise so that it is substantially parallel to the longitudinal axis of connecting structure 30 as shown, for example, in FIGS. 4 and 6, the distal end of camming surface 74 latches in detent 65 in the proximal side of staple holder 60. Tissue 12 is then firmly clamped between anvil 54 and opposing staple holder surface 64. Staple holder 60 and anvil 54 are substantially parallel, and the appropriate spacing is maintained between anvil 54 and surface 64 by pivotal axis 62 and spacer member 66 on the side of staple holder 60 opposite axis 62. Spacer member 66 performs its function by contacting the adjacent portion of anvil 54. Proper alignment of staple holder 60 and anvil 54 is aided by alignment pin 80 (FIG. 6) which extends through the side of staple holder 60 opposite pivotal axis 62 and into alignment aperture 58 in anvil assembly 52 when staple holder 60 is pivoted parallel to anvil 54.

Also when actuator 70 is fully pivoted counter-clockwise as shown in FIGS. 4 and 6, drive pin 76, which is carried by actuator 70, is aligned with drive pin 90 in the proximal section of connecting structure 30. The distal end of drive pin 76 then extends into the proximal side of staple holder 60 and is adjacent the proximal surface of staple driving assembly 68 (FIG. 6) in the staple holder. Safety latch 100 (FIG. 4), which normally keeps actuator lever 110 pivoted counter-clockwise away from handle 20, is now released by pivoting it clockwise down to the broken line position shown in FIG. 4. Lever 110 can now be pivoted clockwise about pivotal axis 112 toward handle 20 (i.e., by squeezing it toward the handle with the fingers of the hand holding the handle) to actuate the staple driving mechanism.

When lever 110 is pivoted clockwise as just described, the end of lever 110 inside the proximal end of connecting structure 30 contacts head 92 on the proximal end of drive pin 90 and drives pin 90 in the distal direction. The distal end of pin 90 in turn contacts head 78 on the proximal end of drive pin 76 and drives that pin in the distal direction (see FIG. 7). The distal end of pin 76 contacts the proximal surface of staple driving assembly 68, thereby driving that assembly in the distal direction and causing it to drive staples 120 out of staple holder 60, through tissue 12, and against anvil 54. Anvil 54 crimps the staples so that they will remain in and hold the tissue. When the staples have thus been crimped, lever 110 is released and returns to its original position under the influence of compression coil return spring 94 (FIGS. 2 and 4) located around the proximal end of drive pin 90 between head 92 and surface 32 in connecting structure 30.

Figure 8:
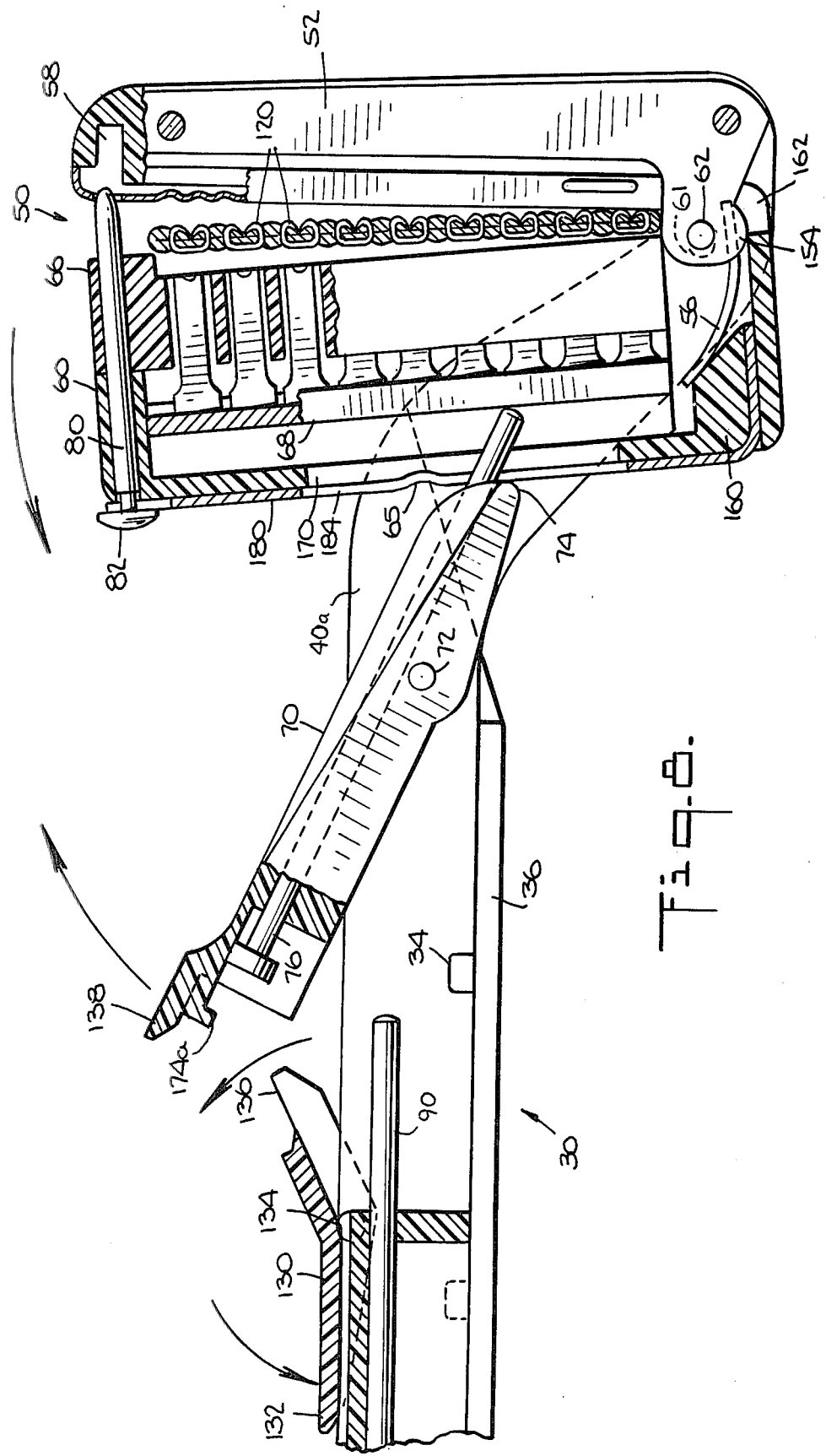
FIG. 8 is a view similar to FIGS. 5-7 showing how the tissue is released from the apparatus after it has been stapled.

The stapling of the tissue is now complete and all that remains to be done is to remove the stapled tissue from the instrument. This is accomplished as shown in FIG. 8 by pressing down on the proximal end 132 of clamp release toggle 130. Clamp release toggle 130 is pivotally mounted on pivotal axis 134 and is located so that its distal end 136 extends under the proximal end 138 of clamp actuator 70. When the proximal end 132 of clamp release toggle 130 is pressed down, the distal end of the toggle raises the proximal end 138 of clamp actuator 70, thereby pivoting clamp actuator 70 clockwise and releasing the pressure of cam surface 74 on staple holder 60. Staple holder 60 then pivots counter-clockwise about pivotal axis 62 in response to the pressure of leaf spring 56. With staple holder 60 thus pivoted back away from anvil assembly 52, the stapled tissue 12 can be readily removed from the instrument.

B. The Actuator Assembly

Instrument 10 may be thought of as having two major components: (1) an actuator assembly comprising handle 20, connecting structure 30, and support structure 40, and (2) staple holder and anvil assembly 50. Additional details regarding assembly 50 are provided in section C below. Similarly, additional details regarding the clamping and staple driving mechanisms which form part of the actuator assembly are provided in section D below. Preliminarily, however, consideration will be given here to some details of the construction of the remainder of the actuator assembly.

In order to make instrument 10 easily and economically disposable, as much of the instrument as possible is preferably made of relatively inexpensive materials such as plastic or the like. Preferably only those parts of the instrument which are subject to high stresses are made of metal.

With the foregoing in mind, the basic elements of support structure 40 are two spaced substantially parallel metal plates 40a and 40b (see, for example, FIGS. 1 and 9). The basic elements of handle 20, on the other hand, are fixed handle member 22 and pivotal actuator lever 110, both principally of plastic. The plastic of handle member 22 is joined to the metal of plates 40a and 40b along connecting structure 30. Plates 40a and 40b extend proximally back from support structure 40 along connecting structure 30 where they are substantially enclosed in and bonded to an outer shell 36 of plastic (see FIGS. 1, 9, and 10). Shell 36 is integral with plastic handle member 22.

Anvil portion 52 of assembly 50 is rigidly mounted between the distal legs 44 of plates 40a and 40b. Staple holder 60 is pivotally mounted on one end of anvil portion 52 between proximal legs 42 of plates 40a and 40b. Clamp actuator 70 and clamp release toggle 130 are also pivotally mounted between the portions of plates 40a and 40b which extend into connecting structure 30. Plates 40a and 40b support the respective opposite ends of the pivotal axes 72 and 134 of elements 70 and 130 (see FIGS. 3, 9, and 10). Also, near the proximal ends of plates 40a and 40b, these plates support the respective opposite ends of pivotal axis 112 of actuator lever 110 (see FIG. 4). Actuator lever 110 contains a metal core 114 (FIGS. 2 and 4) by which lever 110 is mounted on pivotal axis 112 and which extends beyond axis 112 to contact head 92 on drive pin 90.

C. The Staple Holder and Anvil Assembly

As best seen in FIG. 9, anvil portion 52 of staple holder and anvil assembly 50 has a base member 150 which is rigidly and permanently mounted between the distal legs 44 of plates 40a and 40b by rivets 48 (FIG. 2) or comparable means. Anvil 54 is mounted on base member 150 by being fitted or formed over an outwardly flared rail portion 152 (FIG. 9) of base member 150. Anvil 54 has two parallel rows of staple crimping pockets or recesses 54a and 54b (see also FIG. 3). Each row of anvil pockets 54a and 54b is aligned with a respective one of two parallel rows of staples 120 in staple holder 60. Two adjacent staple pockets in each row are respectively aligned with the two points of each staple in the associated row of staples. As best seen for example in FIG. 5, anvil 54 also has a hole 54c for admitting the end of alignment pin 80 into aperture 58 in base member 150 when tissue is clamped in the apparatus. At the other end of the anvil assembly, base member 150 has a proximally extending tongue 154 (FIG. 5) on which staple holder 60 is pivotally mounted as mentioned above and described in more detail below.

Returning again to FIG. 9, staple holder 60 is disposed between the proximal legs 42 of plates 40a and 40b. Staple holder 60 has an outer housing 160 having a pair of tabs 162 (FIG. 5) extending distally on each side of tongue 154. Pivot pin 62 is retained in tongue 154 and extends from each side of the tongue into an elongated aperture 61 in each of tabs 162 to provide the pivotal mounting for staple holder 60 on anvil portion 52. Apertures 61 are elongated in a direction perpendicular to the distal surface of staple holder 60 which contacts the tissue when tissue is clamped in the apparatus (i.e., parallel to the staple driving direction). The ends of pivot pin 62 are initially located in elongated apertures 61 near the proximal ends of those apertures as shown, for example, in FIGS. 2 and 3. As staple holder 60 closes on the tissue being clamped in the apparatus as shown in FIG. 5, elongated apertures 61 allow the portion of staple holder 60 adjacent pin 62 to translate linearly in the proximal direction by a small amount as indicated by the arrow 63 in FIG. 5. This helps prevent the very fluid tissue being clamped from flowing in the direction away from pivotal axis 62 as assembly 50 closes by effectively providing a small amount of linear clamping motion near the end of the predominantly pivotal clamping motion. The tissue is thereby distributed more uniformly in the apparatus. When assembly 50 is fully closed as shown in FIG. 6, the ends of pivot pin 62 bear on the distal ends of elongated apertures 61, thereby cooperating with spacer member 66 to maintain staple holder 60 parallel to anvil portion 52.

Returning once more to FIG. 9, staple holding member 164 is mounted in the distal side of housing 160. Staple holding member 164 has two parallel rows of staple containing apertures 164a and 164b which are respectively aligned with anvil pocket rows 54a and 54b. Each staple containing aperture initially contains one staple 120, and the apertures are further aligned so that one anvil pocket in the associated row of anvil pockets is opposite each point of the staple in that aperture. Behind each staple 120 is a staple pusher 166 slidably mounted in the apparatus (see also FIG. 5). The proximal ends of staple pushers 166 all contact transverse pusher member 168 which is also slidably mounted in the apparatus. Elements 166 and 168 therefore comprise the staple driving assembly 68 in staple holder 60. Access to this staple driving assembly is through elongated slot 170 in the proximal side of housing 160.

Staple holder 60 is normally biased away from anvil 54 as shown, for example, in FIG. 2 by leaf spring 56. As seen in FIG. 5, for example, one end of leaf spring 56 is mounted in tongue 154 on anvil base member 150. The other end of leaf spring 56 bears on surface 172 inside staple holder 60.

Staple holder 60 also carries alignment pin 80. In order to prevent the end of alignment pin 80 from partly obstructing the open end of assembly 50 when that assembly is open and thereby presenting an obstacle and possible hazard to the tissue being placed in or removed from the instrument, alignment pin 80 is reciprocally mounted in staple holder 60 and provided with means for automatically extending the pin when assembly 50 is closed and automatically retracting the pin when assembly 50 is opened. As shown for example in FIG. 3, the proximal end of pin 80 is engaged by the slotted end 182 of leaf spring 180 which extends along the proximal side of housing 160 and is anchored at the bottom of the housing (see FIG. 5). Leaf spring 180 has an elongated slot 184 which is generally co-extensive with slot 170 in housing 160. Leaf spring 180 also has a transverse recess which forms detent 65 for the distal end of camming surface 74 when clamp actuator 70 is pivoted parallel to connecting structure 30. The proximal side of housing 164 may be correspondingly relieved adjacent detent recess 65. Leaf spring 180 is arranged so that it is normally inclined away from the proximal side of housing 160 in the direction toward pin 80 as shown, for example, in FIGS. 2 and 3. In this condition, spring 180 holds pin 80 in the retracted position so that the distal end of the pin does not project from holder 60.

When clamp actuator 70 is pivoted counter-clockwise as shown in FIG. 5 to close assembly 50, camming surface 74 first contacts the central portion of spring 180 on both sides of slot 184. This presses spring 180 against the proximal side of housing 160 as assembly 50 begins to close. The deflection of spring 180 causes pin 80 to move distally of holder 60, thereby causing the distal end of pin 80 to project from holder 60 toward anvil portion 52. As assembly 50 continues to close, the distal end of pin 80 enters alignment aperture 58 in anvil assembly 52 to help keep staple holder 60 and anvil portion 52 aligned as described above. If for any reason spring 180 does not fully seat against the proximal side of housing 160, pin 80 can be pushed home into aperture 58 by pressing on head 82 as indicated by the arrow 186 in FIG. 6. When assembly 50 is opened again as shown in FIG. 8, camming surface 74 moves away from spring 180, thereby allowing spring 180 to move away from the proximal surface of housing 160 and retract pin 80.

It should be noted that the precise alignment between the staple guiding and staple forming elements (i.e., staple holder 60 and anvil 54, respectively) which is required to assure proper staple formation is provided entirely by assembly 50 itself. The tolerance requirements for all other parts of the apparatus (i.e., the actuator) are thereby substantially reduced. This greatly reduces the cost of the actuator and makes possible the extensive use of relatively inexpensive materials in that portion of the apparatus as described above.

As in the case of the remainder of the apparatus, preferably as much of staple holder and anvil assembly 50 as possible is made of relatively inexpensive and economically disposable materials such as plastic or the like. Thus anvil base member 150, staple holder housing 160, and staple containing member 164 are all preferably plastic. The other higher stress elements of assembly 50 such as anvil 54, pivotal axis 62, staple driving assembly 68, alignment pin 80, and springs 56 and 180 are typically metal.

D. The Clamping and Staple Driving Mechanism

Clamp actuator 70 is normally pivoted transversely of longitudinal structure 30 as shown, for example, in FIG. 2 because assembly 50 is normally held open by spring 56 and the proximal side of staple holder 60 therefore tends to pivot actuator 70 clockwise. Prior to use, drive pin 76 is retained in actuator 70 by beads 174a and 174b respectively adjacent the proximal and distal sides of head 78 (see also FIG. 5).

When it is desired to close assembly 50, the operator of the instrument presses down on the proximal end 138 of actuator 70 as shown in FIG. 5, thereby pivoting actuator 70 counter-clockwise until it is substantially parallel to connecting structure 30 (see FIG. 6). As actuator 70 pivots counter-clockwise, camming surface 74 presses against spring 180, thereby causing spring 180 to press against the proximal side of staple holder housing 160 and pivot staple holder 60 toward anvil portion 52. As this takes place, the distal end of pin 76 passes through slot 184 in spring 180 and enters slot 170 in housing 160. When actuator 70 is fully parallel to connecting structure 30 as shown in FIG. 6, and assembly 50 is fully closed, pin 76 is substantially perpendicular to transverse pusher member 168 at approximatey the midpoint of that member. Actuator 70 comes to rest in the position parallel to connecting structure 30 when it contacts surface 34 in connecting structure 30. Actuator 70 remains latched or locked in this position by cooperation of camming surface 74 and detent 65.

Figure 7:
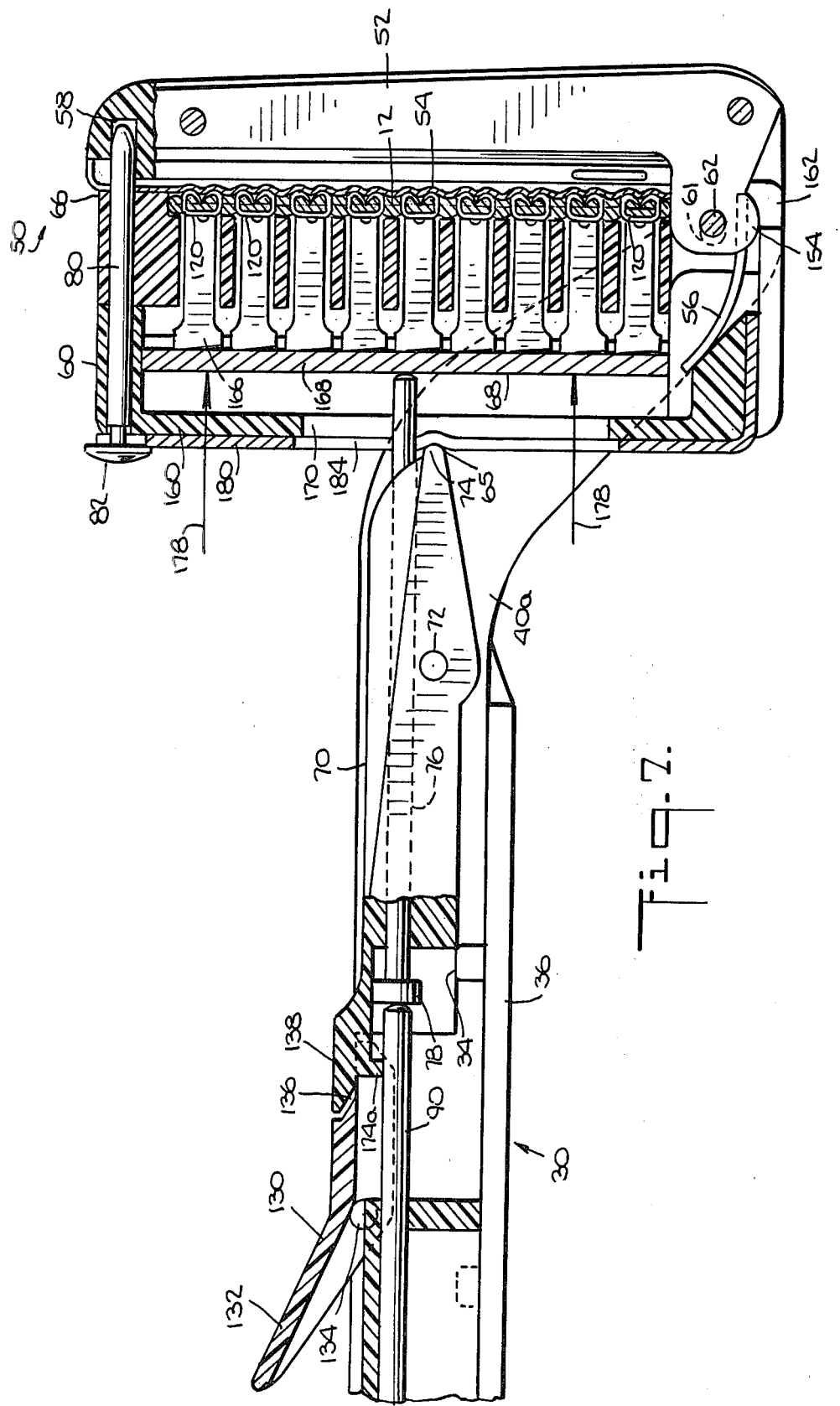
FIG. 7 is a view similar to FIGS. 5 and 6 showing how the apparatus operates to staple the clamped tissue.

Also when actuator 70 is in the position parallel to connecting structure 30, the proximal end 138 of actuator 70 overlies the distal end 136 of toggle 130 and pivots the proximal end 132 of toggle 130 out from connecting structure 30. Pivoting actuator 70 parallel to connecting structure 30 also aligns drive pin 76 with drive pin 90 as mentioned above (see also FIG. 4). Operation of lever 110 then causes pin 90 to drive pin 76 in the distal direction as shown in FIG. 7. The head 78 of pin 76 shears off bead 174b and the proximal end of pin 76 then contacts transverse pusher member 168 in staple holder 60 and drives that member and all of staple pushers 166 in the distal direction as indicated by the arrows 178 in FIG. 7. This simultaneously drives all of staples 120 as described above.

When the staples have been driven and lever 110 has been released, drive pin 90 retracts so that the clamping of the tissue can be released as shown in FIG. 8 by depressing the proximal end 132 of toggle 130. This pivots actuator 70 clockwise to release the pressure of camming surface 74 on spring 180. Staple holder 60 then pivots counter-clockwise in response to the pressure of spring 56, thereby withdrawing the distal end of alignment pin 80 from aperture 58. Spring 180 also flexes back away from the proximal side of housing 160, thereby retracting the distal end of pin 80 into staple holder 60 and leaving the open side of assembly 50 unobstructed for easy removal of the staple tissue from the apparatus.

In the interest of economical disposability, clamp actuator 70 and toggle 130 are both preferably of plastic or the like. Drive pins 76 and 90 are typically metal.

E. Operational Advantages

FIG. 11 shows in solid lines a greatly simplified elevational view of the distal end of a prior art thoracic-abdominal surgical stapler. This instrument includes a frame 200 having a square-cornered U-shaped end portion 210. As in the apparatus of the present invention, the distal leg 214 of this end portion carries the anvil portion of the apparatus. This leg is tied to the remainder of frame 200 by base portion 216 and proximal leg 212. Staple holder 220 in this apparatus is mounted so that it is axially reciprocal in frame 200. Staple holder 220 is translated toward leg 214 to clamp the tissue in the stapler between the staple holder and the anvil. Thereafter, a staple driving mechanism, which is also axially reciprocal in frame 200, is operated to simultaneously drive a plurality of staples out of staple holder 220, through the clamped tissue, and against the anvil carried by leg 214.

The forces exerted in the apparatus of FIG. 11 to clamp the tissue and then simultaneously drive a relatively large number of staples typically cause deflections or deformations of structure 210. These deflections, greatly exaggerated for clarity, are represented by the broken lines in FIG. 11. As indicated by these broken lines, the clamping and stapling forces in the apparatus tend to push leg 214 away from staple holder 220 to the position 214'. Because of the way leg 214 is supported relative to staple holder 220, leg 214 tends to be both shifted transversely down relative to its initial position (deflection measurement A), and also angled out away from staple holder 220 in the direction toward the open side of U-shaped structure 210 (deflection measurement B).

Staple holder 220 may not be able to completely conform to or follow the deflections of leg 214 because it is supported principally for reciprocal motion by the portion of frame 200 remote from leg 214. Accordingly, the above-mentioned deflections of leg 214 tend to cause misalignment between the anvil and the staple holder. Occasionally this misalignment may result in one or more staples being improperly or incompletely formed because the ends of the staple do not enter the anvil pockets properly. Such improperly or incompletely formed staples are highly undesirable because they may injure the tissue, may not hold the tissue securely, and/or may become loose during or after the surgical procedure.

FIG. 12 shows how the apparatus of the present invention overcomes the above-described misalignment problems. As in FIG. 11, the undeflected positions of the various elements are shown in full lines and the deflected positions are shown in broken lines, with the deflections being greatly exaggerated for purposes of illustration. As in the prior art apparatus, the tissue clamping and staple driving forces tend to deflect support structure leg 44 downward and away from its initial position to position 44'. However, because staple holder 60 is mounted entirely by pivotal connection 62 (which displaces to position 62') adjacent one end of leg 44, staple holder 60 displaces with leg 44 to position 60'. Accordingly, staple holder 60 always remains properly aligned with the anvil mounted on leg 44, and the possibility that staples may be improperly formed due to misalignment of the staple holder and anvil is substantially reduced. Staple holder 60 always remains properly spaced from and parallel to the anvil by cooperation of pivotal axis 62 (in contact with the distal ends of elongated apertures 61) and spacer member 66 at the respective opposite ends of staple holder 60. This is also important for proper staple formation.

In addition to substantially reduced potential for misalignment between the anvil and the staple holder, the illustrative embodiment shown in FIGS. 1–10 can be economically produced as a completely disposable item because of the extensive use of relatively inexpensive materials and because of the much less stringent manufacturing tolerances for the actuator portion of the apparatus. By making the apparatus entirely disposable after a single use, all difficulty and expense associated with cleaning and sterilizing between uses is completely eliminated. The embodiment shown in FIGS. 1–10 also has the advantages that it is easier and faster to operate than many prior art thoracic-abdominal staplers. Clamping and release of the tissue is effected rapidly by levers 70 and 130 rather than by threaded mechanisms. Alignment pin 80 also extends and retracts automatically when assembly 50 is first closed and later reopened.

II. Second Illustrative Embodiment: Permanent Actuator with Disposable Staple Holder and Anvil Cartridge FIGS. 13—17 show an alternative embodiment of the invention which may be basically the same as the first embodiment except that staple holder and anvil assembly 50 is made as a disposable cartridge 250, while the remainder of the instrument (i.e., the cartridge actuator) is made in a permanent design which is capable of being cleaned, sterilized, and reused.

As can be seen in FIG. 13, cartridge 250 is substantially identical to assembly 50 in the embodiment described above, and the same reference numbers are applied to the same parts in both embodiments. Thus cartridge 250 includes anvil portion 52 having staple holder 60 pivotally mounted at one end by means of pivotal axis 62. Anvil portion 52 carries anvil member 54 (FIGS. 14 and 16), and staple holder 60 carries alignment pin 80 which is automatically extended and retracted by operation of leaf spring 180 when the cartridge is in use in an instrument. The interior construction and operation of cartridge 250 may be identical to that of assembly 50 and will not be described in detail again.

The actuator 230 with which cartridge 250 is used may be substantially the same as the actuator portion of instrument 10, with the possible exception that more permanent materials may be used for parts which are typically plastic or the like in the disposable instrument. Accordingly, the major portion of actuator 230 will be neither shown nor described again. Only the distal end portion 240 of actuator 230, which differs slightly from the corresponding portion 40 of instrument 10, as shown in FIGS. 13—17 and described in detail below.

As shown for example in FIG. 13, distal end portion 240 of actuator 230 is similar to the corresponding portion 40 of instrument 10, except that portion 240 is designed to removably receive cartridge 250. Structure 240 is made up of two spaced substantially parallel plates 40a and 40b which are connected at the extreme distal end of the actuator by transverse plate 242. Structure 240 defines proximal leg 42, distal leg 44, and base 46, all respectively similar to the corresponding portions of instrument 10.

Anvil portion 52 of cartridge 250 is designed to slide longitudinally into and out of leg 44 of structure 240. The distal side of anvil portion 52 has a distally projecting retaining structure 252 which fits into slot 244 in plate 242 (see also FIGS. 14–16). Retaining structure 252 and slot 244 are designed so that beads 254 (FIG. 15) on retaining structure 252 seat in notches 246 in the sides of slot 244 when cartridge 250 is properly positioned in the instrument. At the same time, beads 248 on the inside surfaces of leg 44 seat in aperture 256 in anvil portion 52. Elements 246, 248, 254, and 256 therefore comprise detent means for releasably retaining cartridge 250 in position in actuator 230. Laterally extending flanges 258 (FIGS. 13 and 16) on retaining structure 252 also help keep anvil portion 52 in position in leg 44 and thereby help hold cartridge 250 in the actuator.

As in instrument 10, when staple cartridge 250 is positioned in actuator 230, stable holder 60 fits between plates 40a and 40b adjacent proximal leg 42 (see FIG. 17). Staple cartridge 250 is operated in the same way that assembly 50 in instrument 10 is operated to clamp and staple tissue inserted between anvil 54 and staple holder 60. When cartridge 250 has been used, it is removed from actuator 230 by pulling anvil portion 52 out of leg 44. The expended cartridge is discarded and another cartridge is loaded in the actuator if additional stapling is required during the surgical procedure. When the surgical procedure is complete, actuator 230 is cleaned and sterilized to prepare it for use in another surgical procedure.

It is to be understood that a cartridge 250 of the type shown in FIGS. 13-17 can be used in actuators having many designs other than the particular actuator design referred to above. For example, cartridge 250 could be used in a screw operated actuator of the type described below. Many actuators having combinations of screw and lever operation are also known in the art and are adaptable for use with the staple holder and anvil cartridge of this invention.

Like assembly 50 in instrument 10, the precise alignment of staple holder 60 and anvil 54 in cartridge 250 is maintained entirely by cartridge 250 itself. This is particularly advantageous when cartridge 250 is to be used with a permanent and reusable actuator because the actuator then no longer requires precise tolerances. The actuator is therefore more tolerant of possibly rough handling during cleaning, sterilizing, and storage.

III. Third Illustrative Embodiment: Disposable Instrument with Screw Operated Actuator FIGS. 18–22 show another illustrative embodiment of the invention in which a staple holder and anvil assembly similar to those described above is actuated by a screw actuator. This apparatus may be made either as a completely disposable unit analogous to the first embodiment described above, or a disposable staple holder and anvil cartridge similar to cartridge 250 may be removably mounted in an actuator of permanent and reusable design in a manner analogous to the second embodiment described above. For purposes of illustration it will be assumed that the apparatus of this embodiment is entirely disposable, and it will be readily apparent from the description given herein how this apparatus can be modified to comprise a permanent actuator for accepting disposable cartridges.

As shown for example in FIG. 18, the thoracicabdominal stapler 310 of this embodiment includes handle portion 320 at the proximal end of the apparatus, staple holder and anvil assembly 50 at the distal end of the apparatus, open U-shaped or V-shaped support structure 340 for supporting assembly 50, and a longitudinal connecting shaft portion 330 between handle portion 320 and support structure 340. Staple holder and anvil assembly 50 may be identical to the corresponding portion of the first embodiment and will therefore not be described in detail again. Support structure 340 may also be similar to support structure 40 in the first embodiment, except that it terminates at its proximal end in internally threaded block 342. Thus support structure 340 includes proximal and distal legs 42 and 44 joined by base 46, all respectively similar to the corresponding elements in the first embodiment. Also as in the first embodiment, distal leg 44 supports assembly 50 by way of a rigid connection to anvil portion 52 of that assembly. Staple holder 60 is pivotally mounted on anvil portion 52 by means of a pivotal connection adjacent support structure base 46.

As can be seen more clearly in FIG. 20, shaft portion 330 includes concentric inner and outer shafts 334 and 332, respectively. The distal end of outer shaft 332 is threaded through block 342 and terminates in clamp actuating surface 344 adjacent the proximal side of staple holder 60. Inner shaft 334 has a threaded connection 346 with a portion of the interior surface of outer shaft 332. Inner shaft 334 is mounted in outer shaft 332 so that inner shaft 334 translates longitudinally relative to outer shaft 332 when there is relative rotation between the shafts. The amount of this relative longitudinal translational motion is limited by annular flange or ring 336a on a proximal portion of shaft 334 in cooperation with adjacent annular shoulders 336b and 336c on shaft 332. Initially shaft 334 is retracted so that ring 336a is adjacent shoulder 336b. The proximal end of inner shaft 334 extends beyond the proximal end of outer shaft 332. Inner shaft 334 is prevented from rotating relative to handle portion 320 by flat surfaces 338 on the sides of the proximal end of shaft 334 in cooperation with similar interior surfaces of handle portion 320 (see also FIG. 19). Inner shaft 334 can, however, translate longitudinally relative to handle portion 320. The distal end of inner shaft 334 passes through slot 170 and 184 in the proximal side of staple holder 60 adjacent the midpoint of transverse pusher member 168 and acts as the drive pin for the staple driving mechanism in staple holder 60.

The proximal portion of outer shaft 332 has a radially outwardly extending annular flange 350 having a plurality of apertures 352 extending therethrough parallel to the longitudinal axis of the apparatus. Proximally of flange 350 shaft 332 also has a radially inwardly extending annular groove 354.

Handle portion 320 includes winged handle 322 rotatably mounted on the proximal end of shaft 332. Handle 322 is retained on the end of shaft 332 by pin 324 which extends through a portion of annular groove 354 (see also FIG. 22). Handle 322 is initially prevented from rotating relative to shaft 332 by pin 360 which extends longitudinally through handle 322 and into one of apertures 352 in flange 350. Pin 360 has a pivoting finger ring 362 at its proximal end to allow the operator of the instrument to retract pin 360 at the appropriate time as described below. Flange or ring 364 on pin 360 near its distal end cooperates with shoulder 326 inside the adjacent portion of handle 322 to prevent pin 360 from being retracted substantially more than the amount required to withdraw it from aperture 352 in flange 350.

In operation, handle portion 320 and shaft portion 330 are initially retracted as shown in FIG. 18 so that staple holder 60 is pivoted away from anvil portion 52 and the tissue 12 to be stapled can be inserted between elements 52 and 60. Shaft 334 is also initially retracted relative to shaft 332 so that ring 336a is adjacent shoulder 336b, and pin 360 is seated so that it extends into one of apertures 352 to prevent handle 322 from rotating relative to shaft 332.

When the tissue to be stapled has been positioned in the instrument, handle 322 is rotated clockwise relative to support structure 340 as indicated by the arrows 370 in FIG. 18. Shaft 332 rotates with handle 322 because of the presence of pin 360 in aperture 352. Shaft 334 also rotates with handle 322 because of the rotation transmitting connection 338 between those elements. Accordingly, as handle 322 rotates, shaft assembly 330 rotates with it and the threaded connection between shaft 332 and block 342 causes assembly 330 to translate distally toward staple holder 60. The distal end 344 of shaft 332 bears on the proximal side of staple holder 60, thereby pivoting staple holder 60 clockwise as viewed in FIG. 20 toward anvil portion 52 and clamping the tissue to be stapled in the instrument.

When staple holder 60 is fully pivoted toward anvil portion 52, shoulder 348 on shaft 332 comes to rest against block 342 as shown in FIG. 21. Accordingly, shaft 332 can no longer be advanced and the rotation of handle 322 is stopped. When this occurs the operator of the instrument knows that the tissue is clamped and ready to be stapled. The operator then uses ring 362 to retract pin 360 to the position shown in FIG. 21. This decouples handle 322 from shaft 332 and allows the rotation of handle 322 to continue.

During the further rotation of handle 322, outer shaft 332 remains stationary and only inner shaft 334 rotates with the handle. Because of the threaded connection 346 between shafts 332 and 334, inner shaft 334 translates in the distal direction relative to outer shaft 332. The distal end of shaft 334 therefore drives the staple driving mechanism in staple holder 60 in the same way that pin 76 in the previously described embodiments drives that mechanism.

When the staples have been fully driven as shown in FIG. 21, ring 336a has moved from shoulder 336b to shoulder 336c. This prevents further distal translation of shaft 334 and again stops the clockwise rotation of handle 322. The stapling operation is now complete and all that remains is to remove the instrument from the stapled tissue. This is done by rotating handle 322 in the direction opposite the tissue clamping and staple driving direction to cause shaft 332 to retract from support structure 340 and thereby allow staple holder 60 to pivot counter-clockwise away from anvil portion 52. Retraction of shaft 332 may begin immediately if there is sufficient frictional contact between handle 322 and shaft 332 or if pin 360 is again pushed into one of apertures 352. Otherwise retraction of shaft 332 will begin after shaft 334 has been retracted so that ring 336a contacts shoulder 336b and thereby transmits the rotation of handle 322 to shaft 332.

Elements 322 and 332 in the embodiment shown in FIGS. 18–22 can be of economically disposable material such as plastic or the like. Only the higher stress elements such as elements 324, 334, and 360 and the components of support structure 340 need be of metal. The construction of assembly 50 may be as previously described. Accordingly, the entire apparatus of this embodiment can be readily and economically disposed of after a single use, thereby avoiding all inconvenience and expense of reloading, cleaning, and sterilizing. The embodiment shown in FIGS. 18–22 also has the advantage of being relatively small and compact, which reduces the cost of the apparatus and facilitates its use in certain surgical procedures.

It will be understood that the embodiments shown and described herein are only illustrative of the principles of the invention, and that various modifications can be made by those skilled in the art without departing from the scope and spirit of the invention. For example, although the third embodiment described above is intended to be disposed of after a single use, similar apparatus could be made having a permanent reusable actuator capable of receiving a disposable staple holder and anvil cartridge 250 like that described in connection with the second embodiment above.

I claim:

1. A surgical staple cartridge for use with an actuator assembly including a rigid frame having a U-shaped portion for simultaneously forming a plurality of surgical staples in body tissue comprising:
- an anvil member for clinching surgical staples driven against it;
- a staple holder pivotally connected to the anvil member adjacent one end of the anvil member, the staple holder containing a plurality of surgical staples and including staple driving means for simultaneously driving all of the staples from the staple holder; and
- means associated with the anvil member for allowing the cartridge to be removably mounted on the actuator frame so that the anvil member is adjacent a first leg of the U-shaped portion, so that the pivotal connection between the anvil member and the staple holder is adjacent the base of the U-shaped portion, and so that the staple holder is adjacent a second leg of the U-shaped portion, the staple holder being movable relative to the frame when the cartridge is thus mounted on the frame so that when the staple holder is pivoted away from the anvil member, the tissue to be stapled can be positioned between the anvil member and the staple holder via the open side of the U-shaped portion.

2. The cartridge defined in claim 1 further comprising spring means acting between the anvil member and the staple holder for resiliently pivoting the staple holder away from the anvil member.

3. The cartridge defined in claim 1 for use with an actuator assembly further including clamp actuator means for pivoting the staple holder toward the anvil member to clamp the tissue, the cartridge further comprising spacer means located adjacent the side of the cartridge opposite the pivotal connection between the anvil member and the staple holder for maintaining a predetermined minimum spacing between the staple holder and the anvil member when the staple holder is pivoted toward the anvil member by the clamp actuator means.

4. The cartridge defined in claim 1 further comprising alignment means located adjacent the side of the cartridge opposite the pivotal connection between the anvil member and the staple holder for aligning the staple holder and anvil member in a direction parallel to the pivotal axis when the staple holder is pivoted toward the anvil member to clamp the tissue to be stapled between the staple holder and the anvil member, the alignment means comprising surface portions associated with each of the anvil member and the staple holder, the surface portions being substantially perpendicular to the pivotal axis and being substantially rigid in a direction parallel to the pivotal axis, the surface portions associated with the staple holder contacting the surface portions associated with the anvil member when the staple holder is pivoted toward the anvil member to clamp the tissue.

5. The cartridge defined in claim 4 wherein the alignment means comprises a pin substantially perpendicular to the pivotal axis which extends into both the staple holder and the anvil member when the staple holder and anvil member are pivoted toward one another to clamp the tissue.

6. The cartridge defined in claim 1 wherein the means for allowing the cartridge to be removably mounted on the frame comprises detent means mounted on the anvil member for cooperating with the frame to releasably retain the anvil member on the frame.

7. A surgical staple cartridge for use with an actuator assembly for simultaneously forming a plurality of surgical staples in body tissue comprising:
- an anvil member;
- a staple holder pivotally mounted adjacent one end of the anvil member, the staple holder containing a plurality of surgical staples and including staple driving means for simultaneously driving all of the staples from the staple holder; and
- alignment means associated with the side of the cartridge opposite the pivotal mounting for aligning the staple holder and anvil member on the associated side of the cartridge, the alignment means comprising a pin which extends into both the staple holder and the anvil member when the staple holder and anvil member are pivoted toward one another, and means for normally retracting the pin so that it normally does not extend into the area between the staple holder and the anvil member.

8. The cartridge defined in claim 7 for use with an actuator assembly including clamp actuator means for pivoting the staple holder toward the anvil member, the cartridge further comprising first spring means acting between the anvil member and the staple holder for resiliently pivoting the staple holder away from the anvil member, and wherein the means for normally retracting the pin comprises second spring means mounted on the staple holder for contact by the clamp actuator means when the clamp actuator means is operated to pivot the staple holder toward the anvil member, the spring constants of the first and second spring means being chosen so that, when the clamp actuator means is operated to contact the second spring means and to pivot the staple holder toward the anvil member, the second spring means allows the pin to extend into the area between the staple holder and the anvil member before the first spring means allows the staple holder to pivot fully toward the anvil member.

9. A surgical stapling cartridge for use in a surgical stapler for forming a plurality of surgical staples in body tissue, the stapler including a rigid frame having a normally open peripheral portion for admitting body tissue to be stapled into an interior region of the frame, the cartridge comprising:
- a longitudinal anvil member having opposite first and second ends;
- a staple holder pivotally mounted on the first end of the anvil member, the staple holder containing a plurality of surgical staples and including staple driving means for driving the staples from the staple holder; and
- means associated with the anvil member for removably mounting the anvil member on the frame adjacent one side of the interior region of the frame with the second end of the anvil member adjacent the normally open peripheral portion, with the first end of the anvil member remote from the normally open peripheral portion, and with the staple holder adjacent the side of the interior region of the frame opposite the anvil member.

10. The cartridge defined in claim 9 further comprising:
- an alignment pin reciprocally mounted on the side of the staple holder opposite the pivotal mounting, the alignment pin being substantially perpendicular to the pivotal axis of the pivotal mounting and also substantially perpendicular to the longitudinal axis of the anvil member when the staple holder is pivoted closest to the anvil member, the alignment pin being extendable into an aperture in the second end of the anvil member when the staple holder is pivoted closest to the anvil member; and first spring means for resiliently retracting the alignment pin in a direction away from the anvil member so that the alignment pin normally does not extend into the region between the staple holder and the anvil member.

11. The cartridge defined in claim 10 further comprising second spring means acting between the staple holder and the anvil member adjacent the pivotal mounting for resiliently pivoting the staple holder away from the anvil member, the spring constants of the first and second spring means being chosen so that when the staple holder is pivoted toward the anvil member by a force applied to the first spring means, the first spring means allows the alignment pin to extend into the region between the staple holder and the anvil member before the second spring means allows the staple holder to pivot fully toward the anvil member.

12. An assembly for use in a surgical stapler for simultaneously forming a plurality of surgical staples in body tissue comprising:

a longitudinal anvil member;

a staple holder pivotally mounted relative to the anvil member on a pivotal axis transverse to the longitudinal axis of the anvil member adjacent one end of the anvil member, the staple holder containing a plurality of surgical staples oriented so that they point toward the anvil member when the staple holder is pivoted toward the anvil member, and the staple holder including means for simultaneously driving the staples from the staple holder in the direction of the anvil member when the staple holder is pivoted toward the anvil member;

an alignment pin associated with the side of the assembly opposite the pivotal axis and extendable into both the staple holder and the anvil member to align the staple holder and the anvil member on the associated side of the assembly; and means for normally retracting the alignment pin so that it does not extend into the area between the staple holder and the anvil member when not needed to align the staple holder and the anvil member.

13. The apparatus defined in claim 12 wherein the alignment pin is reciprocally mounted in the staple holder substantially perpendicular to the pivotal axis and transverse to the longitudinal axis of the anvil member and wherein the means for normally retracting the alignment pin comprises spring means associated with the staple holder for normally retracting the alignment pin into the staple holder in a direction away from the anvil member.

14. A surgical stapler for simultaneously forming a plurality of surgical staples in body tissue comprising:

a rigid frame having a U-shaped portion;

an anvil member mounted on a first leg of the U-shaped portion so that the anvil member is stationary relative to the frame;

a staple holder disposed adjacent the second leg of the U-shaped portion and being pivotally mounted adjacent one end of the anvil member, the pivotal mounting being adjacent the base of the U-shaped portion, the staple holder containing a plurality of surgical staples and including means for simultaneously driving the staples from the staple holder; and actuator means mounted on the frame for pivoting the staple holder toward the anvil member and actuating the means for driving the staples from the staple holder.

15. The apparatus defined in claim 14 wherein the staple holder further includes an alignment pin substantially perpendicular to the pivotal axis of the pivotal mounting, the alignment pin being reciprocally mounted on the side of the staple holder opposite from the pivotal mounting and being extendable from the staple holder toward the anvil member; wherein the anvil member includes a rigid aperture for receiving the end of the extended alignment pin when the staple holder is pivoted toward the anvil member, the extended alignment pin contacting the rigid sides of the aperture to help align the staple holder and the anvil member on the side of the staple holder opposite from the pivotal mounting; and wherein the actuator means includes clamp actuator means mounted on the frame for operating on the side of the staple holder remote from the anvil member to pivot the staple holder relative to the frame toward the anvil member and extend the alignment pin.

16. The apparatus defined in claim 15 wherein the alignment pin is reciprocated by a leaf spring which extends along the side of the staple holder remote from the anvil member and wherein the clamp actuator means contacts the leaf spring to extend the alignment pin from the staple holder toward the anvil member when the clamp actuator means operates to pivot the staple holder toward the anvil member.

17. The apparatus defined in claim 16 further comprising spring means acting between the staple holder and the anvil member for resiliently pivoting the staple holder away from the anvil member, the spring constants of the spring means and the leaf spring being chosen so that when the clamp actuator means operates to pivot the staple holder toward the anvil member the alignment pin extends from the staple holder toward the anvil member before the spring means allows the staple holder to pivot fully toward the anvil member.

18. The apparatus defined in claim 14 wherein the frame includes a longitudinal member rigidly connected to the second leg of the U-shaped portion, the longitudinal member extending substantially perpendicular to the second leg and lying in the plane of the U-shaped portion, and wherein the actuator means comprises:

clamp actuator means mounted on the longitudinal member for operating on the side of the staple holder remote from the anvil member to pivot the staple holder toward the anvil member; and staple actuator means mounted on the longitudinal member for operating on the means for driving the staples from the staple holder.

19. The apparatus defined in claim 18 wherein the clamp actuator means comprises a first lever pivotally mounted on the longitudinal member adjacent the side of the staple holder remote from the anvil member; wherein the staple actuator means comprises a second lever pivotally mounted on the longitudinal member adjacent the first lever; and wherein the actuator means further comprises a linkage mounted on the first lever for operatively connecting the second lever to the means for driving the staples only when the first lever has pivoted the staple holder toward the anvil member so that the second lever is inoperative until the first lever has been operated.

20. The apparatus defined in claim 19 wherein the clamp actuator means further comprises:
   means for releasably locking the first lever in the position which pivots the staple holder toward the anvil member; and
   toggle means mounted on the longitudinal member for releasing the first lever from the locked position.

21. The apparatus defined in claim 18 wherein the clamp actuator means comprises a first actuator member threadedly mounted on the longitudinal member adjacent the side of the staple holder remote from the anvil member for pivoting the staple holder toward the anvil member when the first actuator member is rotated relative to the longitudinal member; and wherein the staple actuator means comprises a second actuator member threadedly mounted on the first actuator member adjacent the side of the staple holder remote from the anvil member for operating on the means for driving the staples from the staple holder when the second actuator member is rotated relative to the first actuator member.

22. The apparatus defined in claim 21 wherein the actuator means further comprises:
   handle means rotatably mounted on the first actuator member;
   first coupling means for selectively rotatably coupling the handle means to the first actuator member to cause the first actuator member to rotate with the handle means when the first coupling means is engaged; and
   second coupling means for rotatably coupling the handle means to the second actuator member to cause the second actuator member to rotate with the handle means and with the first actuator member when the first coupling means is engaged, and to cause the second actuator member to rotate with the handle means and relative to the first actuator member when the first coupling means is not engaged.

23. The apparatus defined in claim 14 wherein the anvil member and the staple holder comprise an assembly which is removably mounted on the frame.

24. The apparatus defined in claim 14 wherein the staple holder is pivotally mounted on the anvil member and wherein the pivotal mounting between the anvil member and the staple holder comprises:
   pivot pin connection means between the anvil member and the staple holder; and
   an aperture in at least one of the anvil member and the staple holder for receiving the pivot pin connection means and having a dimension parallel to the direction in which the staples are driven larger than the corresponding dimension of the pivot pin connection means to allow some linear translation of the staple holder relative to the anvil parallel to the direction in which the staples are driven.

25. A surgical stapling instrument comprising:
   frame means having a normally open peripheral portion for admitting tissue to be stapled into an interior region of the frame means;
   staple driving means for stapling tissue located in the interior region of the frame means;
   actuator means for causing the staple driving means to staple the tissue located in the interior region of the frame means; and
   means responsive to the actuator means for closing the normally open peripheral portion of the frame means to enclose the tissue to be stapled in the interior region of the frame means and thereby prevent tissue from escaping from the interior region via the normally open peripheral portion during stapling, the means for closing the normally open peripheral portion of the frame means comprising a staple holder pivotally mounted relative to the frame means at a location remote from the normally open peripheral portion and pivotally biased so that the staple holder normally does not obstruct the normally open peripheral portion, the staple holder responding to the actuator means by pivoting so that it spans the normally open peripheral portion.

26. The apparatus defined in claim 43 wherein the staple holder includes a spacer member at a location remote from the pivotal mounting of the staple holder for contacting a portion of the frame means opposite the staple holder when the staple holder is pivoted to span the normally open peripheral portion and for maintaining a gap between the remainder of the staple holder and the portion of the frame means opposite the remainder of the staple holder.

27. The apparatus defined in claim 25 wherein the means for closing the normally open peripheral portion of the frame means further comprises an alignment member retractably mounted on the staple holder adjacent the normally open peripheral portion of the frame means and being extendable from the staple holder into the normally open peripheral portion, the alignment member being biased so that it normally does not extent from the staple holder into the normally open peripheral portion, the alignment member responding to the actuator means by extending from the staple holder into the normally open peripheral portion and into a portion of the frame means opposite the staple holder.

28. A surgical staple cartridge for use with a actuator assembly for simultaneously forming a plurality of surgical staples in body tissue comprising:
   an anvil member; and
   a staple holder pivotally mounted adjacent one end of the anvil member, the staple holder containing a plurality of surgical staples and including staple driving means for simultaneously driving all of the staples from the staple holder, the pivotal mounting of the staple holder comprising:
   pivot pin connection means between the anvil member and the staple holder; and
   an aperture in at least one of the anvil member and the staple holder for receiving the pivot pin connection means and having a dimension parallel to the staple driving direction larger than the corresponding dimension of the pivot pin connection means to allow some linear translation of the staple holder relative to the anvil parallel to the staple driving direction.

29. An assembly for use in a surgical stapler for simultaneously forming a plurality of surgical staples in body tissue comprising:
   a longitudinal anvil member; and
   a staple holder pivotally mounted relative to the anvil member on a pivotal axis transverse to the longitudinal axis of the anvil member adjacent one end of the anvil member, the staple holder containing a plurality of surgical staples oriented so that they point toward the anvil member when the staple holder is pivoted toward the anvil member, and the staple holder including means for simultaneously driving the staples from the staple holder in the direction of the anvil member when the staple holder is pivoted toward the anvil member, the pivotal mounting between the anvil member and the staple holder including:

pivot pin connection means between the anvil member and the staple holder; and an aperture in at least one of the anvil member and the staple holder for receiving the pivot pin connection means and having a dimension parallel to the staple driving direction larger than the corresponding dimension of the pivot pin connection means to allow some linear translation of the staple holder relative to the anvil parallel to the staple driving direction.

30. An actuator for supporting and actuating a surgical stapling cartridge including an anvil member and a staple holder pivotally mounted adjacent one end of the anvil member and containing at least one surgical staple, the actuator comprising:

a rigid frame including a substantially U-shaped portion having first and second legs connected by a base;

first means associated with the first leg of the frame of releasably engaging and supporting the anvil member so that the anvil member is aligned with the first leg, the pivotal mounting of the staple holder is adjacent the base, and the staple holder is adjacent the second leg;

second means associated with the second leg of the frame for pivoting the staple holder substantially parallel to the anvil member; and third means associated with the second leg of the frame for actuating the staple holder to drive the staples from the staple holder and against the anvil member.

31. The method of applying a plurality of surgical staples to body tissue comprising the steps of:

placing a disposable surgical stapling cartridge in an actuator, the cartridge including an anvil member and a staple holder pivotally mounted adjacent one end of the anvil member and containing a plurality of surgical staples, and the actuator including a frame for supporting the anvil member and means associated with the frame for pivoting the staple holder relative to the anvil member and driving the staples from the staple holder;

positioning the actuator, with the staple holder pivoted away from the anvil member, relative to the body tissue to be stapled so that the body tissue is between the anvil member and the staple holder;

operating the actuator to pivot the staple holder substantially parallel to the anvil member so that the body tissue is clamped between the staple holder and the anvil member;

operating the actuator to drive the staples from the staple holder, through the clamped body tissue, and against the anvil member to crimp the staples and thereby staple the tissue;

operating the actuator to pivot the staple holder away from the anvil member to release the stapled body tissue from the cartridge; and removing the cartridge and the actuator from the stapled tissue.

32. The method defined in claim 31 further comprising the step of removing the cartridge from the actuator and discarding the cartridge.

33. The method of claim 32 further comprising the step of placing a new disposable surgical stapling cartridge in the actuator in preparation for repeating the preceeding steps.

* * * * *

UNITED STATES PATENT AND TRADEMARK OFFICE
CERTIFICATE OF CORRECTION

PATENT NO. : 4,354,628
DATED : October 19, 1982
INVENTOR(S) : David T. Green

It is certified that error appears in the above—identified patent and that said Letters Patent is hereby corrected as shown below:

| Column | Line | |
|--------|------|---|
| 20 | 17 | "43" should be --25-- |
| 20 | 33 | "extent" should be --extend-- |
| 20 | 39 | "a" should be --an-- |

Signed and Sealed this

Twelfth Day of April 1983

[SEAL]

Attest:

GERALD J. MOSSINGHOFF

Attesting Officer        Commissioner of Patents and Trademarks